US009510912B2

(12) United States Patent
Bencteux et al.

(10) Patent No.: US 9,510,912 B2
(45) Date of Patent: Dec. 6, 2016

(54) MODULE FOR DRIVING A ROBOTIC CATHETERISATION SYSTEM

(71) Applicant: ROBOCATH, Rouen (FR)

(72) Inventors: Philippe Bencteux, Bois-Guillaume (FR); Sébastien Deboeuf, Herblay (FR); Jacques Marignier, Le Mesnil Esnard (FR)

(73) Assignee: ROBOCATH, Rouen (FR)

( * ) Notice: Subject to any disclaimer, the term of this patent is extended or adjusted under 35 U.S.C. 154(b) by 0 days.

(21) Appl. No.: 14/769,667

(22) PCT Filed: Mar. 6, 2014

(86) PCT No.: PCT/FR2014/050515
§ 371 (c)(1),
(2) Date: Aug. 21, 2015

(87) PCT Pub. No.: WO2014/135808
PCT Pub. Date: Sep. 12, 2014

(65) Prior Publication Data
US 2016/0008076 A1    Jan. 14, 2016

(30) Foreign Application Priority Data
Mar. 7, 2013   (FR) ...................................... 13 52058

(51) Int. Cl.
*A61B 19/00*   (2006.01)
*A61M 25/01*   (2006.01)

(52) U.S. Cl.
CPC ........... *A61B 19/2203* (2013.01); *A61B 34/30* (2016.02); *A61M 25/0113* (2013.01); *A61M 25/0147* (2013.01); *A61B 2034/301* (2016.02)

(58) Field of Classification Search
CPC .................................................. A61B 19/2203
(Continued)

(56) References Cited

U.S. PATENT DOCUMENTS

| 6,096,004 A | 8/2000 | Meglan |
| 7,927,310 B2 | 4/2011 | Bencteux et al. |

(Continued)

FOREIGN PATENT DOCUMENTS

| EP | 0 970 633 A1 | 1/2000 |
| EP | 1 792 638 A2 | 6/2007 |

(Continued)

OTHER PUBLICATIONS

French Search Report Application No. PCT/FR2014/050515 reported on Apr. 28, 2014.

*Primary Examiner* — David S Luo
(74) *Attorney, Agent, or Firm* — Miller, Matthias & Hull LLP

(57) ABSTRACT

The invention relates to a module for driving a robotic catheterization system, comprising a base and mobile equipment that rotates in relation to the base about a rotational axis, and comprising a support receiving a flexible medical body; a device for driving in translation, suitable for generating a translation of said body in the main direction; a regulating device comprising a push element which is mobile in relation to the receiving space in a lateral adjustment direction perpendicular to the main direction; and a system for transferring motive energy comprising a control part carried by the base and a transmission part carried by the mobile equipment, the motive energy transfer system being suitable for moving the push element irrespective of the relative orientation of the mobile unit and the base.

17 Claims, 13 Drawing Sheets

(58) Field of Classification Search
USPC .......................................... 318/560, 34, 558
See application file for complete search history.

(56) References Cited

U.S. PATENT DOCUMENTS

| | | | |
|---|---|---|---|
| 8,282,328 B2* | 10/2012 | Gardner | B25C 5/15 |
| | | | 174/159 |
| 2007/0123070 A1 | 5/2007 | Bencteux et al. | |
| 2013/0172738 A1 | 7/2013 | Bencteux et al. | |
| 2013/0231678 A1 | 9/2013 | Wenderow | |

FOREIGN PATENT DOCUMENTS

| | | |
|---|---|---|
| EP | 2 567 670 A1 | 3/2013 |
| WO | WO 2011/109283 A1 | 9/2011 |

* cited by examiner

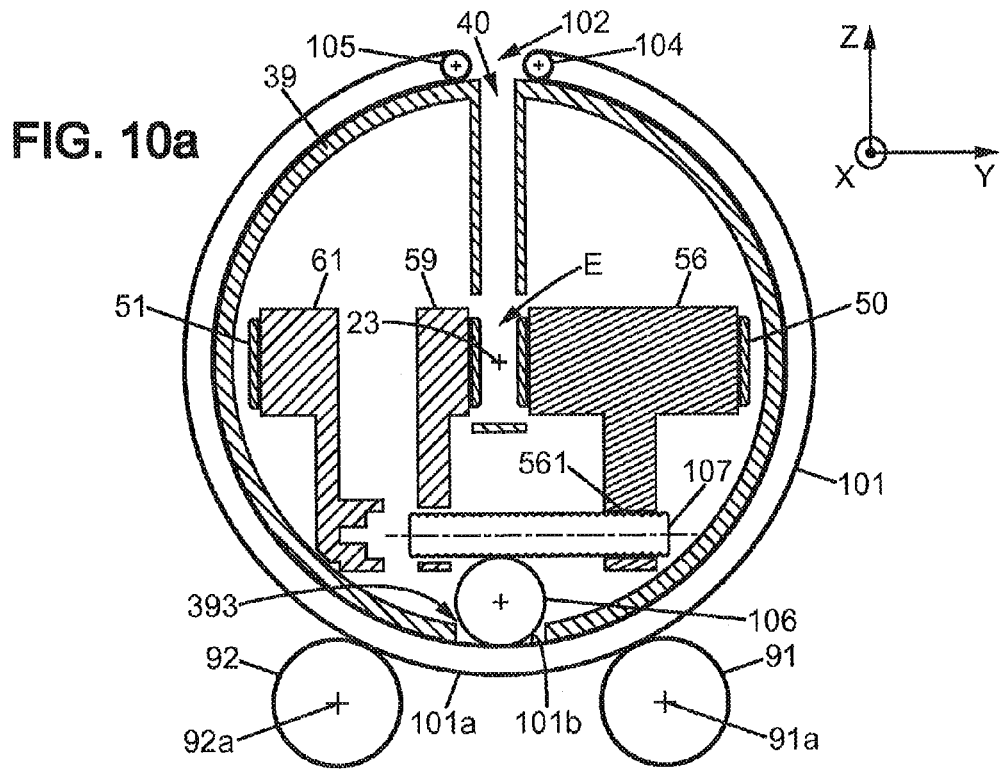
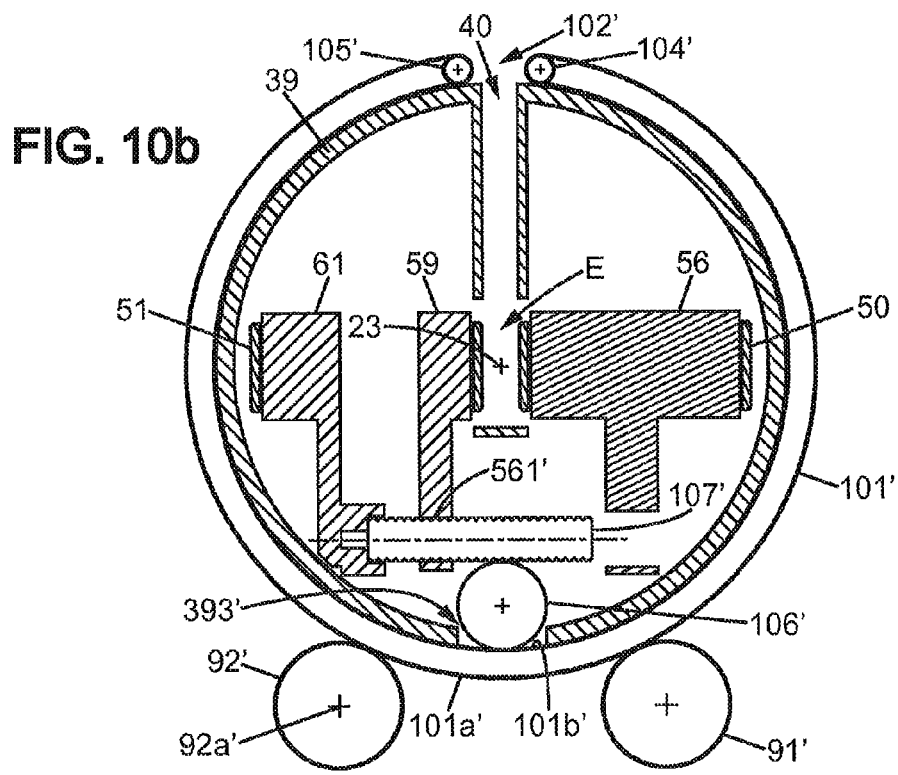

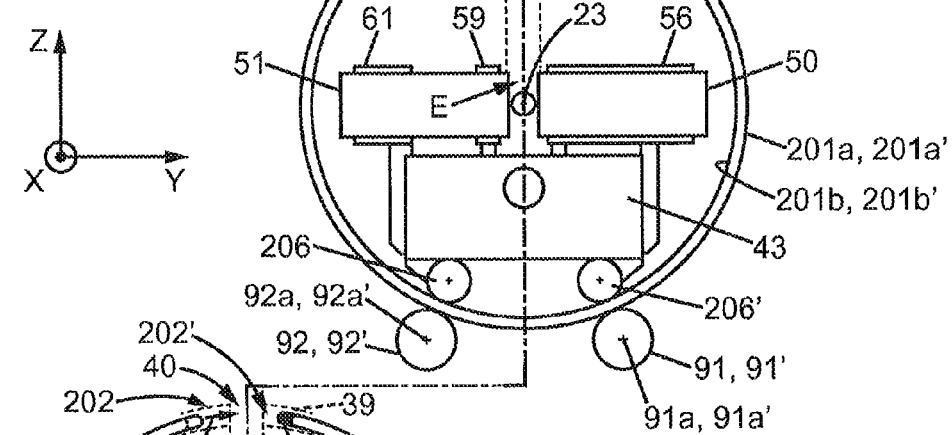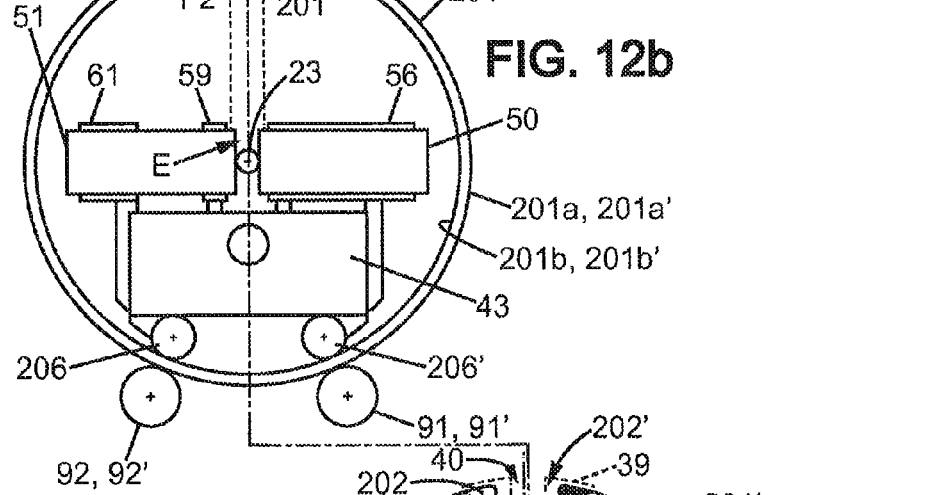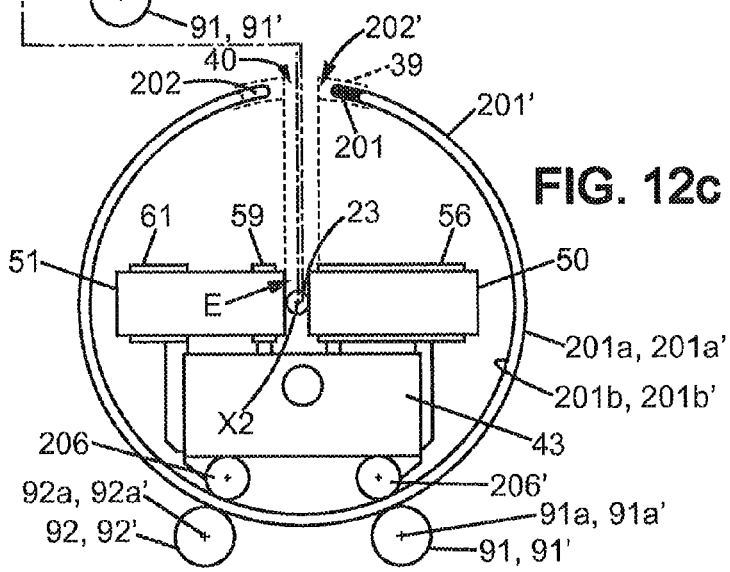

MODULE FOR DRIVING A ROBOTIC CATHETERISATION SYSTEM

CROSS-REFERENCE TO RELATED APPLICATION

This Application is a 35 USC §371 US National Stage filing of International Application No. PCT/FR2014/050515 filed on Mar. 6, 2014, and claims priority under the Paris Convention to French Patent Application No. 13 52058 filed on Mar. 7, 2013.

FIELD OF THE DISCLOSURE

The present invention relates to modules for driving a robotic catheterization systems.

BACKGROUND OF THE DISCLOSURE

A catheter is a typical example of an elongate flexible medical member to be introduced into the body of a patient. Such a catheter is introduced into a tubular anatomical opening of a patient, and therefore must be relatively flexible. The catheter tip must also reach a patient's internal organ, so therefore must be relatively elongated.

Manual insertion of a catheter, or more generally a flexible elongate medical member, into the body of a patient, for example into a tubular anatomical opening, is a relatively standard medical procedure. However, as this procedure is generally monitored by X-rays, the practitioner is exposed to a certain amount of radiation when performing such insertions repeatedly.

To reduce the risks to the practitioner related to repeated irradiation by X-rays, efforts have been made to automate such insertion so that this procedure can be carried out by a robot controlled by the practitioner remotely, still under X-ray guidance but from a room not exposed to the radiation. Such automation is complex, as retaining a grip on the catheter is problematic because it is bathed in preservative liquid such as normal saline solution and must remain sterile. In addition, it must be possible to alternate between rotational and translational movements of the catheter in a completely reliable manner, to enable the practitioner to conduct an examination.

Finally, it is also desirable for such a drive module to work with catheters of different diameters or with other elongate flexible medical members, such as a guide, of smaller diameter than a catheter and generally placed inside the catheter to serve as a guide for the catheter to slide on, or an interventional catheter, also arranged inside the catheter, having a tip providing some medical function such as a surgical tool (clamp, balloon, etc.).

There is therefore a need to develop drive modules that can reliably grip a catheter or other flexible elongate medical members and reliably drive their translational and rotational movements, and that are able to adapt to the varying dimensions of such members.

Recently, a drive system for managing both the translation and rotation of the catheter was proposed in document U.S. Pat. No. 7,917,310. In the system according to this document, the catheter is carried and retained on a plate rotatably mounted on a base to impart rotational motion to the catheter. The plate itself is provided with a mechanism to impart linear motion to the catheter, as well as a biasing wheel associated with an adjustment knob for adapting the drive mechanism to different catheter diameters. The drive system according to this document makes use of external motors, permanently fixed to the frame and associated with systems for transferring linear and rotational motion to the catheter.

However, in the system according to this document, adjustment of the biasing wheel must necessarily be done manually by the practitioner, in an area that may be difficult to access, and located in a room subject to X-ray irradiation, which is not satisfactory in view of the resulting problems outlined above.

Therefore, a need exists to develop catheter drive modules in which adaptation to the procedures concerned can be performed remotely by the practitioner when he or she is located in a room not exposed to X-rays.

The present invention is intended to overcome some or all of these disadvantages.

SUMMARY OF THE DISCLOSURE

For this purpose, the invention provides a module for driving a robotic catheterization system, comprising a base and a mobile unit mounted so as to rotate relative to the base about an axis of rotation extending along a main direction, the mobile unit comprising:
  a mounting in which is defined a receiving space extending along the main direction and adapted to receive an elongate flexible medical member;
  a translation driving means, carried by the mounting and comprising a drive element having a driving surface adapted to engage with the flexible medical member so as to generate a translational movement of said medical device along the main direction;

said drive module further comprising an adjustment device comprising:
  a push element that is part of the mobile unit, movable relative to the receiving space along a lateral adjustment direction perpendicular to the main direction and having a push surface engaging with the drive element so as to move the driving surface along the adjustment direction;
  a motive power transfer system comprising a control part carried by the base, adapted to receive motive power from a motive power source integral with the base, and capable of selectively adopting an active adjustment configuration and an inactive configuration, and a transmission part carried by the mobile unit, engaging with the control part in the active adjustment configuration and adapted to convert the motive power into driving force and to transfer said driving force to the push element in order to move said push element along the adjustment direction, and wherein the motive power transfer system is adapted to transfer the driving force to the push element regardless of the relative orientation of the mobile unit and the base about the axis of rotation, when the control part is in the active adjustment configuration.

With these arrangements, the drive module of the invention can overcome the problems related to the transfer of motive power between a motive power source, integral to a fixed part of the module, and a part receiving this motive power, associated with the mobile unit in a rotatable manner relative to the fixed part.

One of the underlying concepts of the invention is to power the movement of an adjustment device, in particular to adapt the drive module to the various members to be driven and to be able to drive them reliably in translation and in rotation, the motor or motors for this adjustment being remotely controlled by the practitioner while he or she is located in a room not exposed to X-rays.

Such a drive module has applications in the following alternatives:
- a first alternative lies the use of one or more external motors integral to a fixed part of the module, particularly the base, capable of generating motive power such as torque and associated with motion transfer devices which allow converting this motive power and transferring a driving force to an adjustment mechanism carried by a mobile unit that is rotatable relative to the fixed part of the module;
- a second alternative consists of employing one or more motors embedded in a mobile unit that is rotatable relative to a fixed part of the module, in particular the base, and transferring a motive power, this time in the form of electric power, by means of motive power transfer devices, between a power source integral to the fixed part and the motor or motors embedded in the mobile unit.

In preferred embodiments of the invention, one or more of the following arrangements may possibly also be used:
- the control part is adapted to be selectively coupled to and uncoupled from the motive power source in order to switch from the active adjustment configuration to the inactive configuration;
- the control part is movable relative to the transmission part, between a first position corresponding to the active adjustment configuration, in which the control part engages with the transmission part, and a second position corresponding to the inactive configuration, in which the control part does not engage with the transmission part;
- the mobile unit is mounted so as to rotate relative to the base about a first axis of rotation, and the receiving space comprises a defined portion at the mounting along a second axis, parallel to the first axis and offset relative thereto, and the adjustment device is adapted to adjust the offset of the first and second axis;
- the transmission part comprises a circular element centered on the axis of rotation of the mobile unit relative to the base and having a radially outer side which engages with the control part in the active adjustment configuration, and a radially inner side, the transmission part further comprising a transmission mechanism engaging with the inner side of the circular element;
- the mounting of the mobile unit extends between first and second ends along the main direction and has an access opening extending between the first and second ends along the main direction, opening on the one hand to the receiving space defined in the mounting and on the other hand to outside the mobile unit in the radial direction, and the circular element of the transmission part has an opening extending for the entire length of the circular element along the main direction, at least a portion of the opening of the circular element being radially aligned with the access opening of the mounting regardless of the position of the push element in the adjustment direction, allowing access to the receiving space of the mounting from outside the mobile unit;
- the control part comprises a plurality of control members of which at least one engages in the active adjustment configuration with the outer side of the circular element that is part of the transmission part, regardless of the relative orientation of the mobile unit and the base about the axis of rotation.

According to a first variant embodiment of the invention, the control part of the motive power transfer system is adapted to receive motive power in mechanical form from a mechanical motive power source, such as a motor.

In preferred embodiments of the first variant of the invention, one or more of the following arrangements may possibly be used:
- the control part comprises a rotary control member which, in the active adjustment configuration, is in a driving relation with the outer side of the circular element;
- the circular element consists of a ring or a belt mounted so as to rotate on the mobile unit about the axis of rotation;
- the circular element consists of a flexible endless belt following a generally C-shaped path centered on the axis of rotation and stationary relative to the mobile unit about said axis of rotation, the opening of the C defining an opening for unobstructed access to the access opening of the mobile unit, and having a radially outer side which engages with the control part in the active adjustment configuration and a radially inner side which engages with the transmission mechanism;

According to a second variant embodiment of the invention, the control part of the motive power transfer system is adapted to receive motive power in electrical form from an electrical motive power source.

Preferably, in this second variant embodiment, the transmission mechanism of the transmission part comprises a motor embedded in the mobile unit, and the motive power transfer system comprises a slip ring comprising a first portion that is part of the control part carried by the base and connected to an electrical power source, and a second portion that is part of the transmission part and connected to the motor, the first portion and second portion being maintained in sliding contact regardless of the relative orientation of the mobile unit and the base about the axis of rotation, when the control part is in the active adjustment configuration.

Furthermore, in preferred embodiments of the invention, one or more of the following arrangements may possibly be employed:
- the translation driving means comprises a first drive element and a facing second drive element, the receiving space extending between said drive elements, each drive element having a driving surface adapted to engage with the flexible medical member,
- and the adjustment device comprises a first push element and a second push element, each part of the mobile unit and each movable relative to the receiving space along the adjustment direction, each push element having a push surface engaging with an associated drive element so as to move the driving surface of said drive element along the adjustment direction;
- the adjustment device comprises a first motive power transfer system and a second motive power transfer system which are associated with each of the push elements;
- when the control part of the first motive power transfer system is in the active adjustment configuration, the transmission part of the first motive power transfer system is adapted to move the first push element towards the second push element so as to adjust the spacing between the driving surfaces of each of the drive elements along the adjustment direction,
- and, when the control part of the second motive power transfer system is in the active adjustment configuration, the transmission part of the second motive power transfer system is adapted to move the first and second push elements jointly along the adjustment direction in a manner that adjusts the offset of the first axis and second axis;

the adjustment device comprises a single motive power transfer system for the two push elements, and, when the control part of said motive power transfer system is in the active adjustment configuration, the transmission part of said motive power transfer system is adapted to, during a first portion of the actuating stroke, move the first push element towards the second push element so as to adjust the spacing between the driving surfaces of each of the drive elements along the adjustment direction, and, during a second portion of the actuating stroke which follows the first portion, to move the first and second push elements jointly along the adjustment direction in a manner that adjusts the offset of the first axis and second axis;

the translation driving means comprises, on each side of the receiving space:

at least first and second pulleys comprising a driving surface and carried by the mounting, an elongate band constituting the drive element and comprising a first side and an opposite second side, the first side engaging with the driving surface of the pulleys, the second side constituting the driving surface adapted to engage with the flexible medical member, the band being tensioned between the pulleys with an elongate portion extending along the receiving space in the main direction, and the push surface of the push element is positioned between the first and second pulleys and engages with the first side of the band.

According to another aspect of the invention, a module is provided for driving a robotic catheterization system, comprising a base and a mobile unit mounted so as to rotate relative to the base about an axis of rotation extending in a main direction, the mobile unit comprising:

a mounting in which is defined a receiving space extending along the main direction and adapted to receive an elongate flexible medical member;

a translation driving means, carried by the mounting and comprising a drive element having a driving surface adapted to engage with the flexible medical member so as to generate a translational movement of said medical device along the main direction, an embedded motor adapted to drive the driving element;

said drive module further comprising a motive power transfer system comprising a slip ring having a first portion carried by the base and adapted to receive electrical power from an electrical power source integral to the base, and capable of selectively assuming an active adjustment configuration and an inactive configuration, and a second portion carried by the mobile unit and connected to the embedded motor, said first portion and said second mobile being maintained in sliding contact regardless of the relative orientation of the mobile unit and the base about the axis of rotation, when said first portion is in the active adjustment configuration.

According to an advantageous feature of the invention, all of the parts of the drive module are consumable and/or sterilizable items.

The consumable items can be discarded after use and replaced with identical items for future use, and the various non-consumable items are parts that can be disassembled and sterilized for future use.

Other features and advantages of the invention will be apparent from the following description of one of its embodiments, given by way of non-limiting example with reference to the accompanying drawings.

BRIEF DESCRIPTION OF THE DRAWINGS

In the drawings:

FIG. 10a shows a section view along line Xa of the drive module of FIG. 9, and FIG. 10b shows a section view along line Xb of the drive module of FIG. 9, FIGS. 12a to 12c are partial schematic views illustrating the operation of an adjustment device according to the embodiment of FIG. 11.

DETAILED DESCRIPTION OF THE DISCLOSURE

In the various figures, the same references designate identical or similar elements.

Figure 1:
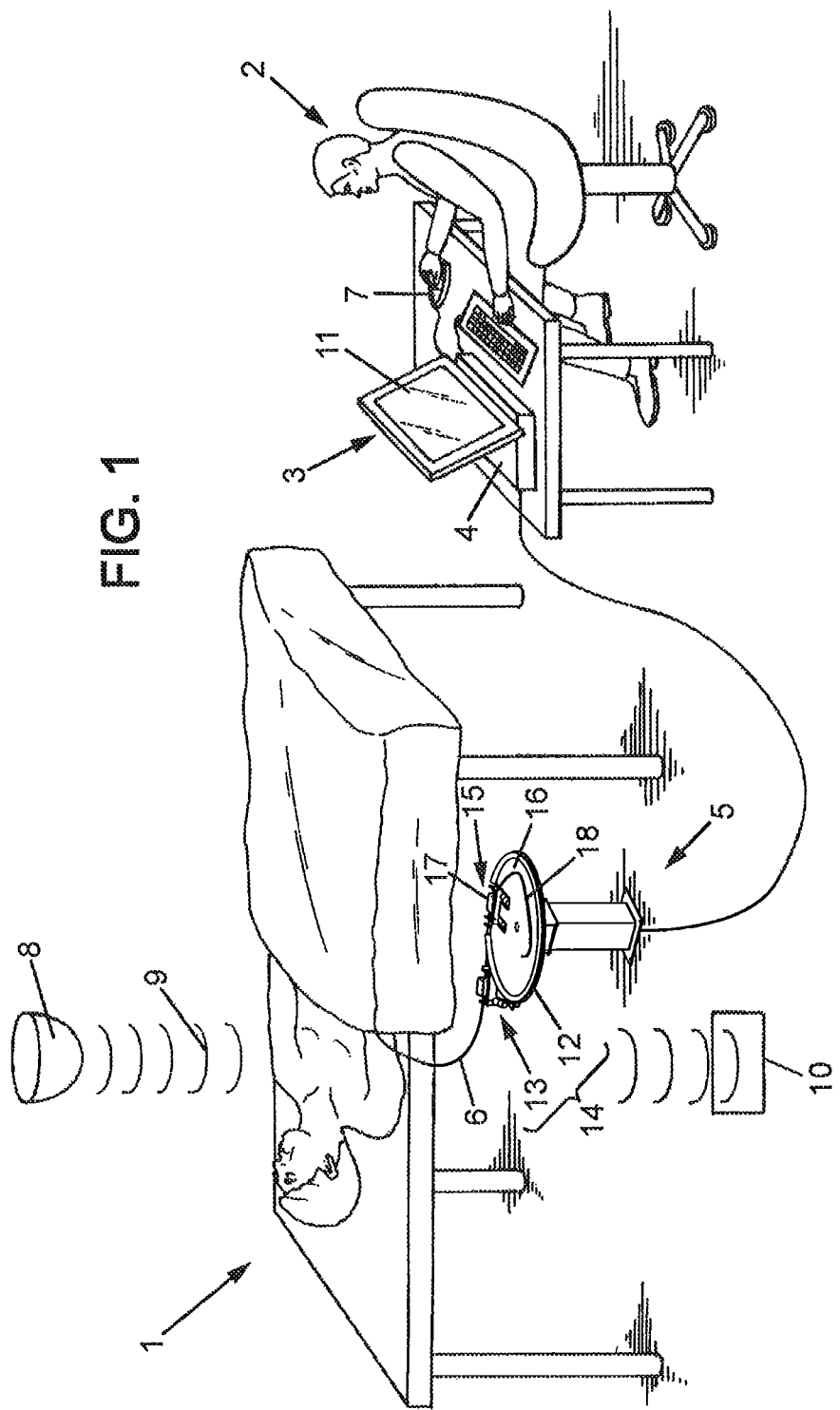
FIG. 1 shows an example system for automated arteriography.

FIG. 1 illustrates an example of a medical system. A patient 1 is lying on an examination table, and there is medical personnel 2, such as a surgeon, performing an automated catheterization (this can also be referred to as robotic catheterization). The catheterization is automated via a computerized unit 3 comprising a central processing unit 4 (processor, logical or otherwise) remotely controlling a robot 5 positioned near the patient 1. The robot 5 is also sometimes referred to as a "winder/unwinder".

The robot 5 is adapted for moving an elongate flexible medical member 6 inside the patient's body 1, under the control of the computerized unit 3. "Elongate flexible medical member" denotes a flexible member that is longitudinally elongated and that can be inserted into a tubular passage of a patient, particularly an artery or vein of a patient, such as a catheter in the conventional sense of the term, a guide wire for guiding such a catheter, or an interventional catheter comprising medical equipment such as a balloon, a gripping or surgical tool, etc.

The robot can be automatically controlled by the computerized unit according to a predefined program, or by medical personnel 2 via a user interface 7 such as a mouse, keyboard, joystick, or similar device.

Such catheterization is monitored by imaging, in particular X-ray imaging. As can be seen in this FIG. 1, there is therefore an X-ray source 8, 9 emitting an X-ray beam toward the patient 1, as well as an X-ray detector 10 arranged beyond the patient in the direction of the X-ray beam emission, able to detect transmission of the X-ray beam through the patient. The imaging system can be connected to the computerized unit 3 so that the image obtained by the imaging system is visible on a screen 11 that is part of the computerized unit 3. Alternatively, the radiographic image is displayed on a dedicated screen.

The medical personnel 2 can thus control the catheterization while viewing on the screen 11 the position of the elongate flexible medical member within the patient's body 1 in relation to the various organs of the patient, which allows controlling various movements of the elongate flexible medical member, by means of the robot 5, such as the two main movements which are the translation (linear motion) of the elongate flexible medical member in either direction longitudinally (advancing or withdrawing) and/or the rotation of the elongate flexible medical member about its longitudinal direction, in one direction of rotation or the other.

The robot 5 will be described in more detail below. It mainly comprises a receptacle 12 within which the elongate flexible medical member can be contained in a sterile manner. For example, the receptacle 12 is a tube open at one end, which holds the elongated flexible medical body immersed in a sterile liquid such as normal saline solution. The elongate flexible medical member exits through an end of the receptacle 12, and engages with a drive module carried by the robot 5 and described in more detail below. The drive module 13 can receive various commands from the computerized unit 3, which include a command to move the elongate flexible medical member translationally along the longitudinal direction, and a command to rotate about this direction. Note that, where appropriate, the robot may receive a command comprising a combination of a translation command and a rotation command in different proportions, and if appropriate, a judicious combination of two commands allows ordering a purely translational movement or purely rotational movement of the elongate flexible medical member by simple resolution of mathematical equations.

Note that the robot 5 can be more complex if such is appropriate.

In particular, the robot 5 can be used for controlling two medical devices such as an elongate flexible medical member (as described above) and a guide threaded inside the flexible elongate medical member. Thus the robot 5 comprises, in addition to the first system 14 described above which comprises both the receptacle 12 and the drive module 13, a second system 15 comprising a receptacle 16 and a drive module 17 for the medical device contained in the receptacle 16. Similarly, the second system 15 cooperates with the first 14, with the end of the second system 15 connected to the receptacle 12 of the first system 14, and more particularly to the back end of the elongate flexible medical member 6. Thus, the guide 18 can be moved within the elongate flexible medical member 6. Drive module 17 is similar to drive module 13, apart from the adaptation to the diameter of the member to be driven, and will not be specifically described. The robot 5 is controlled by the computerized unit 3 so that drive module 17 controls the translation of the guide 18 in its longitudinal direction, and the rotation about this direction. Receptacle 16 is, for example, a basin holding a preservative liquid for storing the guide 18. If necessary, a third system of a similar design (not shown) can be used, nested within the second.

Figure 2:
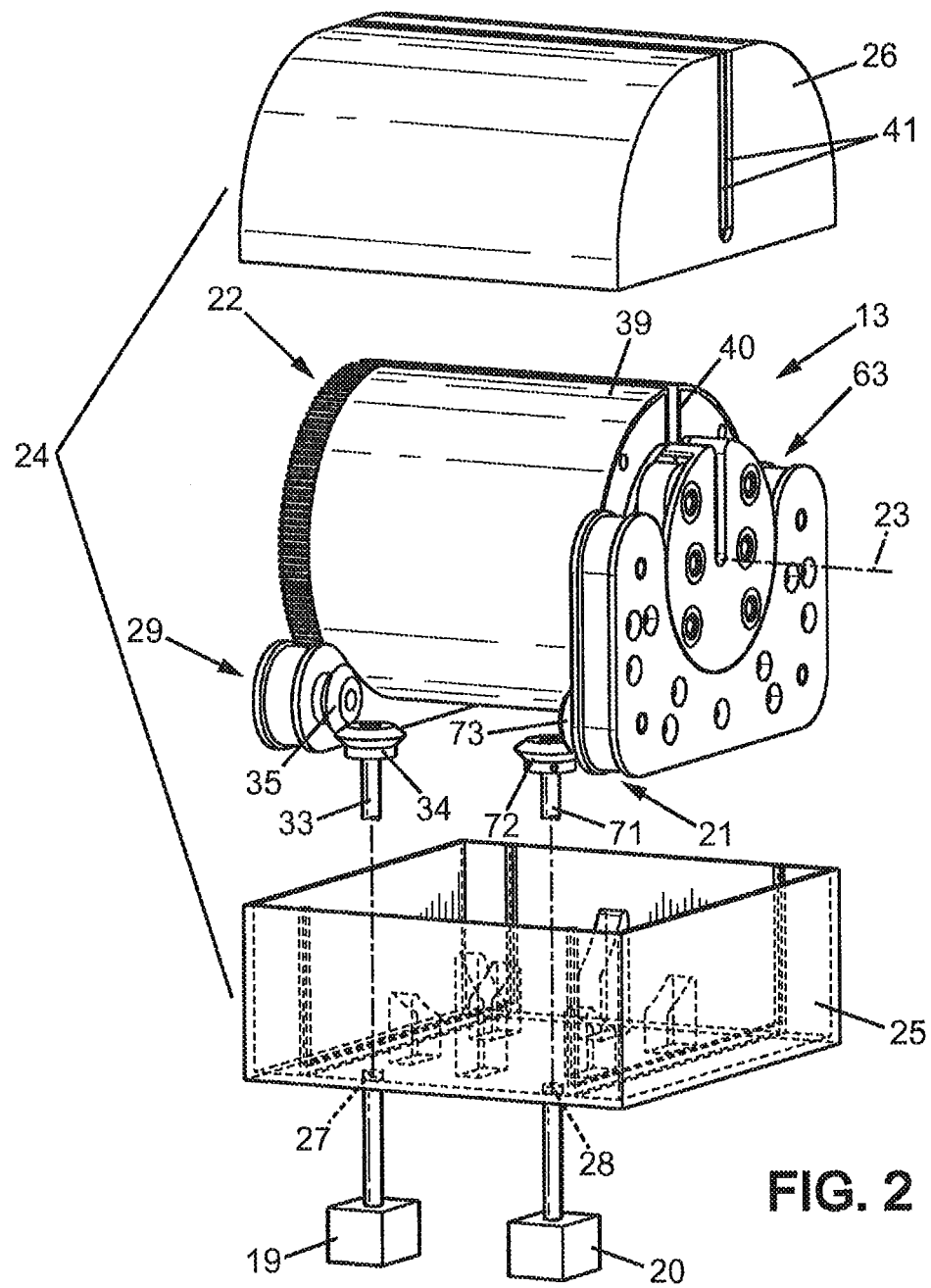
FIG. 2 is an exploded perspective view of a drive module according to a first embodiment.

A first example of a drive module 13 will now be described with reference to FIG. 2. A distinctive feature of the drive module 13 is that is has no embedded motors. The motors are fixed and the motions to impart to the elongate flexible medical member are transferred by a transfer system. Two motors 19 and 20 are thus provided, independently controllable by the computerized unit 3. Motor 19 is intended to control rotation of the elongate flexible medical member 6. Motor 20 is intended to control translation of the elongate flexible medical member 6.

Another distinctive feature of the drive module 13 is that a single module controls both the rotational and translational movements of the elongate flexible medical member. This is achieved in practice by providing a fixed base 21 for the drive module, integral to the motors 19 and 20. The fixed base 21 supports a mobile unit 22 adapted to rotate on the base 21 about an axis 23 extending in the main direction X. In this example, axis 23 coincides with the longitudinal direction of the elongate flexible medical member 6 to be driven. As will be explained in more detail below in various embodiments, the mobile unit supports a system 120 for gripping the elongate flexible medical member 6 which, when not driven, allows rotation of the mobile unit 22 relative to the base 21 to result in rotational movement of the elongate flexible medical member 6 about the main direction X, or when driven, results in translational movement of the elongate flexible medical member 6 in the main direction X.

The drive module 13 comprises a housing 24 which receives the base 21 and the mobile unit 22, and provides basic protection from external contaminants. The housing 24 comprises a lower receptacle 25 and an associated cover 26. The receptacle 25 and the cover 26 can be associated (by fitting one inside the other or by some other means) to surround a substantially closed space containing the base 21 and the mobile unit 22. The receptacle 25 comprises two passages 27 and 28 which can respectively be traversed by a rotation control shaft 33 and a translation control shaft 71, respectively connected to the rotation motor 19 and the translation motor 20.

Figure 7:
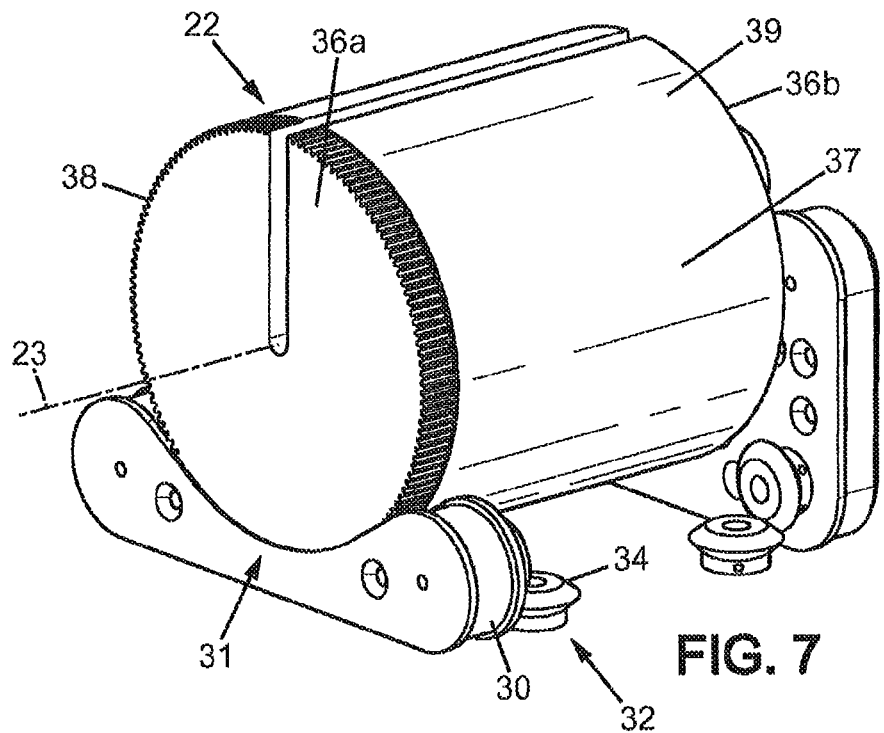
FIG. 7 is a rear perspective view of the system of FIG. 2, FIGS. 8a, 8b, and 8c are front views of the system of FIG. 3, in different driving configurations.

The base 21 contains part of a rotational movement control system 29. In particular, the rotational movement control system 29 imparts, to the mobile unit 22, a rotational movement about axis 23. This system 29 is particularly visible in FIG. 7. In particular, according to this embodiment, the system 29 comprises an endless belt 30 movable along a path comprising a driving portion forming an arc of a circle, the center of the circle coinciding with the axis 23. A guide system 31 guides the belt 30 along this path. A mechanical transfer system 32 is provided for driving the belt 30 along its path. In particular, it may be arranged for example that the end of the rotation control shaft 33 comprises a gear 34 meshing with a gear 35 driving the belt 30. In particular, a mechanical transfer system 32 comprising a right-angle drive transfer may be provided.

The mobile unit 22 comprises a housing 39 extending along the main direction between two end faces 36a and 36b. The housing 39 comprises an outer peripheral surface 37 defining an almost fully closed right circular cylinder about axis 23. The outer peripheral surface 37 comprises, for example, a right circular cylindrical driving surface 38 about axis 23, and engaging with the belt 30. For this engaging, it may be arranged for example that the belt 30 has a toothed face and that the driving surface 38 has a complementary toothed surface, the driving relation of the two toothed surfaces being such that movement of the belt 30 causes the housing 39 to rotate about axis 23.

Referring again to FIG. 2, the housing 39 is not fully closed, and comprises an access opening 40 extending substantially between the two end surfaces 36a and 36b. In particular, the access opening 40 extends continuously along the main direction X. In particular, the access opening 40 also extends along the driving surface 38. The access opening 40 is wide enough to allow insertion or removal of an elongate flexible medical member 6 into or from the housing 39. In addition, two lips 51 of elastomer may be provided that block the access opening 40 when the cover 26 is attached to the receptacle 25 around the base 21 and the mobile unit 22, preventing contaminants from entering said access opening but deformable to allow insertion or removal of an elongate flexible medical member 6.

Figure 5:
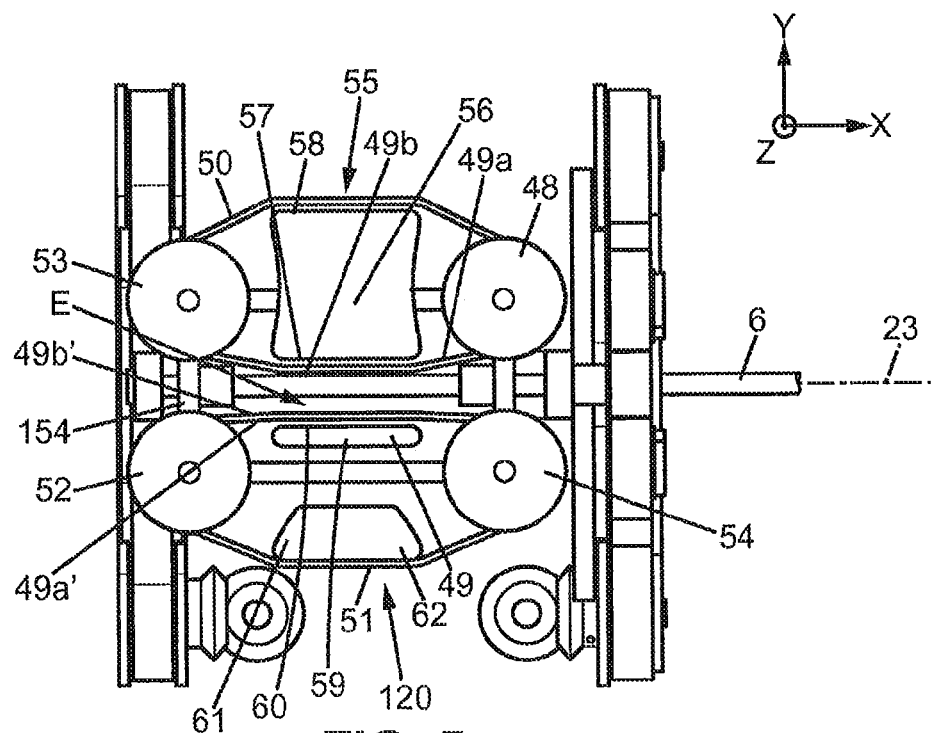
FIG. 5 is a top view of the system of FIG. 3.
Figure 6:
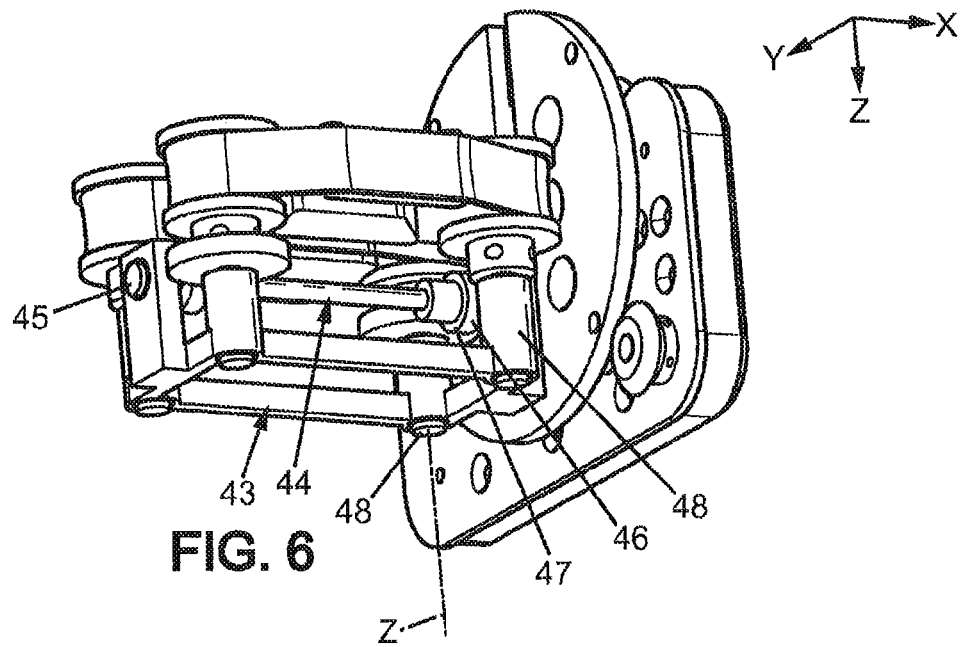
FIG. 6 is a bottom perspective view of the system of FIG. 3.

Referring now to FIGS. 5 and 6, a translation driving means 120 for the elongate flexible medical member 6 according to an exemplary embodiment will now be described. The translation driving system 120 comprises a frame 43 fixed to the housing 39 (not shown in these FIGS. 5 and 6). This frame 43 defines a receiving space E centered on the axis of rotation 23 and adapted to receive the flexible medical member 6. The frame 43 further comprises a set of arms or other structural elements acting as bearings for the various shafts rotatably supported by the frame. The frame 43 accommodates a rotation driving system on one side and part of a translation driving system on the other. These two sides are separate along axis 23. The frame 43 also accommodates, between the rotation driving system and part of the translation driving system along the axis of rotation, a transmission part (not shown in these FIGS. 5 and 6) that is part of an adjustment device which will be described in more detail below.

The frame 43 supports a drive shaft 44 via an end bearing 45 and a second end bearing 46 at the opposite end. The drive shaft 44 extends along the main direction X substantially parallel to axis 23 but offset relative thereto in a transverse direction Z. It extends between a first end that rotates within end bearing 45, and a second end protruding beyond bearing 46. In addition, the shaft 44 comprises at least one gear 47 concentric with the axis of the shaft 44, for rotating a translation driving member 48 for the elongate flexible medical member 6 placed within the receiving space E. In this example, the translation driving member 48 for the elongate flexible medical member 6 comprises a pulley integral with a shaft mounted on the frame 43 so as to be rotatable about an axis normal to the main direction X, meaning the transverse direction Z. The translation driving member 48 is operatively coupled to a driving surface 49b that is part of a drive element and is placed in contact with the elongate flexible medical member 6, such that the rotation of the translation driving member about the transverse direction Z moves the elongate flexible medical member 6 translationally along axis 23. In the example shown, there are in particular driving surfaces 49b, 49b' which are carried by elongate bands, here belts 50 and 51 arranged one on either side of the elongate flexible medical member 6 and forming drive elements for the flexible medical member 6. The belts 50 and 51 are endless belts driven by the rotation of a respective translation driving member 48, 52. For example, a translation driving member 48 as described above is used to drive belt 50, and a similar member 52 is used to drive belt 51. Member 52 is arranged diagonally to member 48 in a rectangle whose other two vertices contain driven pulleys 53 and 54. Thus, on one side translation driving member 48 and driven pulley 53 receive belt 50. On the other side, driving member 52 and driven pulley 54 receive belt 51. Translation driving member 52 also cooperates with the shaft 44, via a transfer gear 154 supported by the shaft 44.

Thus, in the illustrated embodiment, the translation driving member 120 for the elongate medical member 6 comprises, on each side of the receiving space E defined in the frame 43, a first driving pulley 48, 52 and a second driven pulley 53, 54, the first and second pulley 48, 52 having a driving surface and being carried by the frame 43, and an elongate band in the form of a belt 50, 51 constituting the translation driving member for the elongate flexible medical member 6 and having a first face 49a, 49a' engaging with the driving surface of the pulleys 48, 52, 53, 54, and an opposite second face 49b, 49b' constituting the driving surface adapted to engage with the flexible medical member 6, the elongate band in the form of a belt 50, 51 being taut between the pulleys 48, 52, 53, 54 with an elongate portion extending along the receiving space E of said medical member 6.

Alternatively, a system of belts is not necessarily used; instead there is direct use of member 48 and/or member 52, and a (some) associated counter-member(s), arranged one on either side of the elongate flexible medical member 6 in order to drive translationally member 48 and/or member 52 which then directly form the drive element providing the driving surface intended to engage with the flexible medical member 6.

The main direction X was described above as being that of the translational axis when driving the elongate flexible medical member 6. The transverse direction Z was defined as the direction of the axis between the level of the shaft 44 and the level of the elongate flexible medical member 6. A third direction Y can be defined, the lateral direction, forming a trihedron with the two other directions, and considered below as the adjustment direction.

In the drive module according to the invention, an adjustment device 55 is provided that is adapted for adjusting the position of the driving surfaces 49b, 49b' of the belts 50, 51 in the adjustment direction Y, firstly in order to adjust the spacing between the driving surfaces 49b, 49b' of the translation driving members formed by the belts 50, 51 so as to accommodate the different sizes of flexible medical member 6 to be driven when placed in the receiving space E, and secondly in order to adjust an offset of the axis X2 along which the elongate flexible medical member 6 extends between the driving surfaces 49b, 49b' relative to the axis of rotation 23, while keeping these axes 23 and X2 parallel, within a defined portion of the receiving space E at the mounting, so as to improve the rotation about said axis of rotation 23, as will be described in more detail below.

The adjustment device 55 thus comprises a first push element 56, movable along the adjustment direction Y and comprising a push surface 57, placed between the first and the second pulley 48, 53 supporting the belt 50 with which it is associated, and engaging with the inner face 49a of said associated belt 50. Movement of the push element 59 along the adjustment direction Y will move driving surface 49b of belt 50 laterally relative to driving surface 49b' of the facing belt 51. One can thus clasp an elongate flexible medical member 6 placed in the receiving space E, between the two belts 50 and 51. By continuing this movement of the push element 56 towards the facing belt 51 along the adjustment direction Y, one can adjust the offset of axis X2 along which the elongate flexible medical member 6 extends between the driving surfaces 49b, 49b' of belts 50 and 51 relative to the axis of rotation 23, in order to improve the rotation.

The first push element 56 also comprises a tensioning surface 58 intended for tensioning the belt 50. The first push element 56 comprises for example, in the lateral direction, a front face providing the push surface 57 and a rear face opposite the front face. The rear face provides the tensioning surface 58, which cooperates with the belt on the return side. Thus, regardless of the lateral offset imposed by the first push element 56 on the corresponding span, the belt 50 remains tensioned.

On the side opposite the first push element 56 relative to the elongate flexible medical member 6, the adjustment device 55 comprises a second push element 59 which cooperates with inner face 49a' of belt 51. Push element 59 may be movable in the lateral direction Y. This second push element 59 comprises a push surface 60 opposite push surface 57, arranged between the first and second pulleys 52, 54 supporting belt 51 with which it is associated, and engaging with the inner face 49a' of said associated belt 51. The elongate flexible medical member 6 is clasped by belts 50 and 51 between these two push surfaces 57 and 60. The lateral offset of the axis of the elongate flexible medical member 6 may be imposed by the first push element 56 and cause lateral displacement of the second push element 59 in direction Y by means of the elongate flexible medical member 6, against an opposing biasing means (not shown).

Alternatively, and as will be described below, the adjustment device 55 may be adapted to allow moving the first push element 56 towards the second push element 59 in the adjustment direction Y in order to adapt the spacing between the driving surfaces 49b, 49b' of belts 50 and 51 to the elongate flexible medical member 6 to be driven, and to allow moving the first and second push elements 56 and 59 jointly in the adjustment direction Y in order to adjust the offset of axis X2 along which the elongate flexible medical member 6 extends between the driving surfaces 49b, 49b' of belts 50 and 51, relative to the axis of rotation 23, in order to improve the rotation.

On this same opposite side, a tensioner 61 is provided which, together with push surface 60, keeps belt 51 taut, an elastic member such as a spring (not shown) extending between the second push element 59 and the tensioner 61 in the lateral adjustment direction Y.

Thus, as can be understood from the above description, installing the elongate flexible medical member 6 in the mobile unit comprises placing the elongate flexible medical member 6 in the receiving space E between the two belts 50 and 51. The clamping of the elongate flexible medical member 6, and the lateral offset of the axis of the elongate flexible medical member relative to axis 23, are obtained by operating the adjustment device, meaning by adjusting the lateral position of the first and second push elements 56 and 59 by means of the adjustment device 55.

Once the elongate flexible medical member 6 is in position and clamped and/or offset as expected, movement of the elongate flexible medical member 6 along axis 23 is controlled by simple rotation of the drive shaft 44. Rotation of the drive shaft 44 relative to the frame 43 about its axis, parallel to axis 23, causes rotation of at least the rotation driving member 48 about its own axis (transverse axis) due to meshing. In practice, in the present case, rotation of the drive shaft 44 relative to the frame 43 about its axis, parallel to axis 23, also causes rotation of the rotation driving member 52 about its own axis (transverse axis) due to meshing with the transfer gear 154. Rotation driving member 48 drives belt 50, the driving surface 49b thereof then being subjected, at the interaction with the elongate flexible medical member 6, to a translational movement parallel to axis 23. Rotation driving member 52 drives belt 51, the driving surface 49b thereof then being subjected, at the interaction with the elongate flexible medical member 6, to a translational movement parallel to axis 23. These two movements are generated in the same translational direction for the driving surfaces 49b and 49b' (in other words, in opposite directions of rotation of the two belts). The movement of belts 50 and 51 drives the translation of the elongate flexible medical member 6 along axis 23.

To generate a translational movement of the elongate flexible medical member 6, it is therefore sufficient to rotate the shaft 44.

However, as the shaft 44 rotates about axis 23 due to rotation of the mobile unit 22 relative to the base 21 about this axis, while the translation motor 20 remains fixed relative to the base 21, a transfer system 63 needs to be provided which is always connecting the shaft 44 to the motor 20, regardless of the position of the mobile unit 22 relative to this direction. The transfer system 63 comprises a fixed part 64 supported by the base 21, and a mobile part 65 supported by the mobile unit 22. An exemplary embodiment will be provided with reference to FIGS. 2 and 3.

According to this first embodiment, the fixed part 64 comprises a belt 66 which is guided along a closed continuous path. A guide 67 is provided for the belt.

Figure 4:
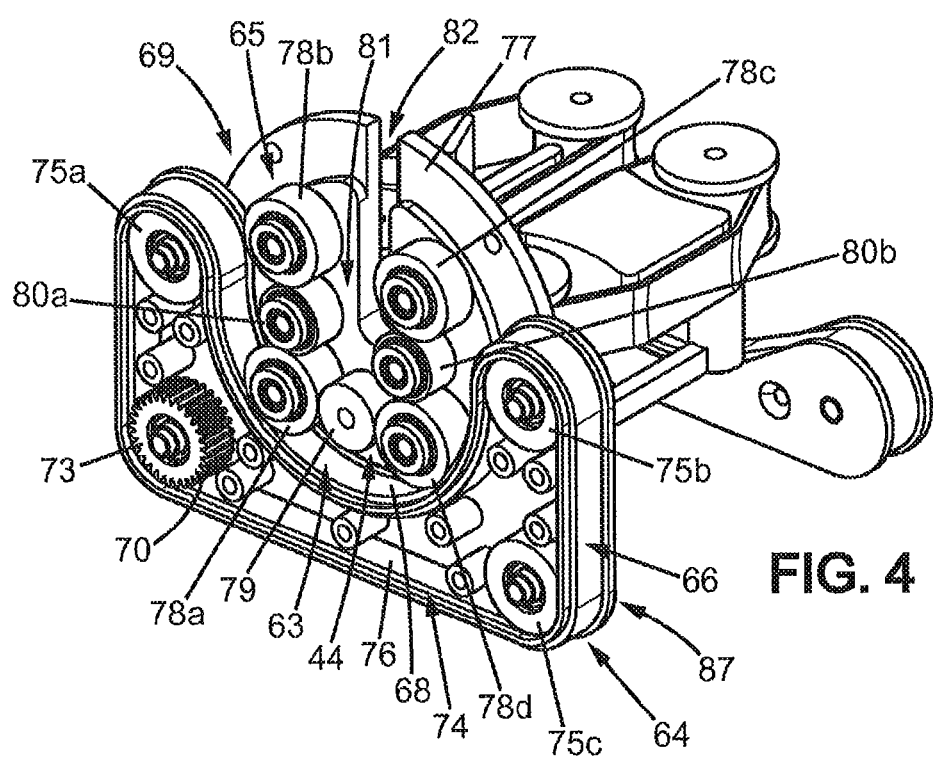
FIG. 4 is a partial view of the system of FIG. 3.

The belt 66 comprises a portion 68 forming an arc of a circle centered on axis 23. This arc portion 68 has a minimum central angle, which will be explained in more detail below, and a maximum central angle which is strictly less than 360°. In particular, the belt 66 defines an access opening 69 large enough to allow passage of the elongate flexible medical member 6. In the particular example represented, the arc portion 68 of the belt 66 has a central angle of about 180°. The belt 66 also comprises a drive portion 70. The drive portion 70 receives the drive command from the translation motor 20. For example, as represented in FIG. 2, the fixed part 64 comprises shaft 71 connected to motor 20, traversing passage 28, and rotating a gear 72 about the vertical axis. The bevel teeth of said gear engage with a gear 73 having an axis parallel to axis 23. That gear 73 engages with the drive portion 70 of the belt as shown in FIG. 4.

The fixed part 64 comprises a set of pulleys adapted to guide the belt 66 so that it moves along a path 74 comprising both the drive portion 70 and the arc portion 68. For example, pulleys 75a, 75b, 75c are provided having parallel axes and arranged to form a rectangle with the gear 73. The path 74 includes three sides of the rectangle, and the arc portion 68 is provided in place of the fourth side. Note that the inner face 76 of the belt 66 is designed to engage with the gear 73 to transfer motion by means of matching shapes, meshing, or other.

The mobile part 65 comprises a support disc 77 integral to the frame 43. The support disc 77, the frame 43, and any other integral part, in particular the housing 39, of the mobile unit 22 forming a frame assembly are denoted as a whole by the term "mounting" 121. The support disc 77 supports a plurality of gears 78a, 78b, 78c, and 78d. These gears 78a-d are each mounted so as to be rotatable relative to the support disc 77 about an axis parallel to the main direction X. In addition, these gears 78a-78d are arranged in a circle centered on axis 23 (therefore concentric with the arc portion 68 of the belt 66). The radius of this circle is smaller than the radius of the arc portion 68 of the belt 66. Each gear 78a-d has its own radius, such that the sum of the radius of the circle and of the radius of the gear 78a-d corresponds to the radius of the arc portion 68 of the belt 66.

Furthermore, each gear 78*a-d* is in a meshing relation with the shaft 44 passing through the support disc 77. For example, a direct meshing relation may be provided, as is the case for the two gears 78*a* and 78*d* which are in direct contact with the head 79 of the shaft 44. There may also be an indirect meshing relation, as is the case for the two gears 78*b* and 78*c* which are in contact with the head 79 of the shaft 44 via the two gears 78*a* and 78*d*.

A system may also be provided for transferring motion between the "indirect" gears 78*b* and 78*c* and the "direct" gears 78*a* and 78*d*, so that they all rotate in the same direction. An intermediate gear 80*a* can thus be provided between gears 78*a* and 78*b*, and an intermediate gear 80*b* between gears 78*c* and 78*d*.

Thus, the support disc 77 carries a mechanized system 78*a*-78*d*, 80*a*-80*b*, which has an access opening 81 aligned with an access opening 82 of the support disc 77. In the present case, the mechanized system has gears arranged in a general U shape, the open side of the U defining the access opening 81. A first arm of the U comprises aligned gears 78*a*, 80*a*, and 78*b*. A second arm of the U comprises aligned gears 78*d*, 80*b*, and 78*c*. Gears 78*a* and 78*d* are arranged one on either side of the head 76 of the shaft 44 to form the base of the U.

In the position represented in FIG. 4, the gears 78*a* and 78*d* are engaged with the belt 66 in the arc portion of the belt. In this position, to drive the elongate flexible medical member 6 translationally along axis 23, gear 73 drives belt 66. Belt 66 rotates gears 78*a* and 78*d* about their own axis relative to the support disc 77 (assuming for clarity that the support disc 77 is unmoving during this operation). Gears 78*a* and 78*d* rotate the shaft via the head 79. Rotation of the shaft 44 causes translation of the elongate flexible medical member by the mechanism described above.

Figure 3:
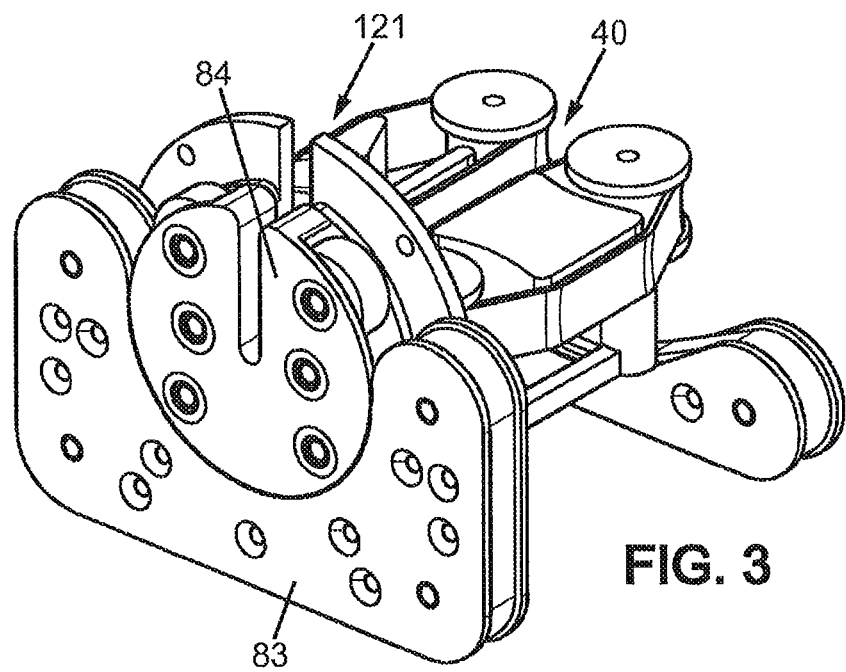
FIG. 3 is a partial view of the system of FIG. 2.

As can be seen in FIG. 3, in actual practice the various mechanisms are hidden and guided by respective covers 83 and 84 for the fixed part and mobile part. The covers have the same access openings as described above, and define bearings for the shafts of the various gears.

As the inner face 76 of the belt is designed to mesh with gear 73, and the opposite outer face 88 is designed to mesh with gears 78*a-d*, each is shaped for such meshing, for example by being provided with teeth that fit with the teeth of the various gears.

Figure 8A:
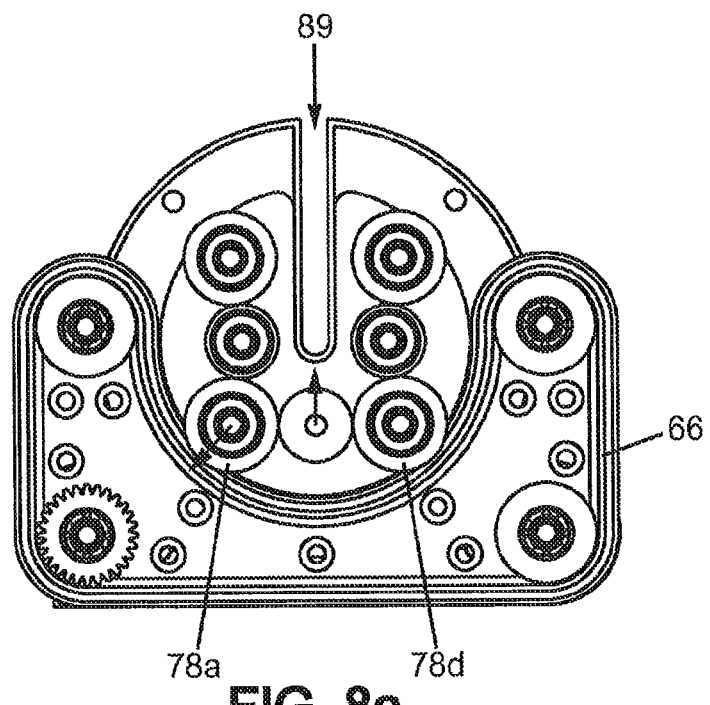

FIG. 8*a* shows an initial position of the drive module. During a preparatory phase, the single access opening 89, formed by the various aligned access openings 81, 82, 40, allows insertion of the elongate flexible medical member into the module, in particular between belts 50 and 51.

To generate a pure translational movement, the rotation driving motor 19 is locked. The translation driving motor 20 is controlled to generate translational movement of the belt 66 along its path. The arc portion 68 causes gears 78*a* and 78*d* to rotate about their axis, which moves the elongate flexible medical member translationally along axis 23. The elongate flexible medical member 6 can be withdrawn at any time via the access openings.

To generate a rotational movement, the rotation driving motor 19 rotates belt 30 which causes the mobile unit 22 to rotate about axis 23. During this movement, gears 78*a* and 78*d* roll on belt 66, until one of the gears, here gear 78*d*, exits the arc portion 68. In addition, it may be desirable to prevent translational movement of the elongate flexible medical member when ordering the rotation. In this case, action is taken so that the relative orientations of the shaft 44 and the elongate flexible medical member 6 within the mobile unit remain unchanged (meaning that the shaft 44 is not rotated relative to the frame 43). This can be achieved by controlling the translation motor so that the belt 66 travels a corresponding distance to prevent any rotation of gears 78*a-d* relative to the support disc 77.

Figure 8B:
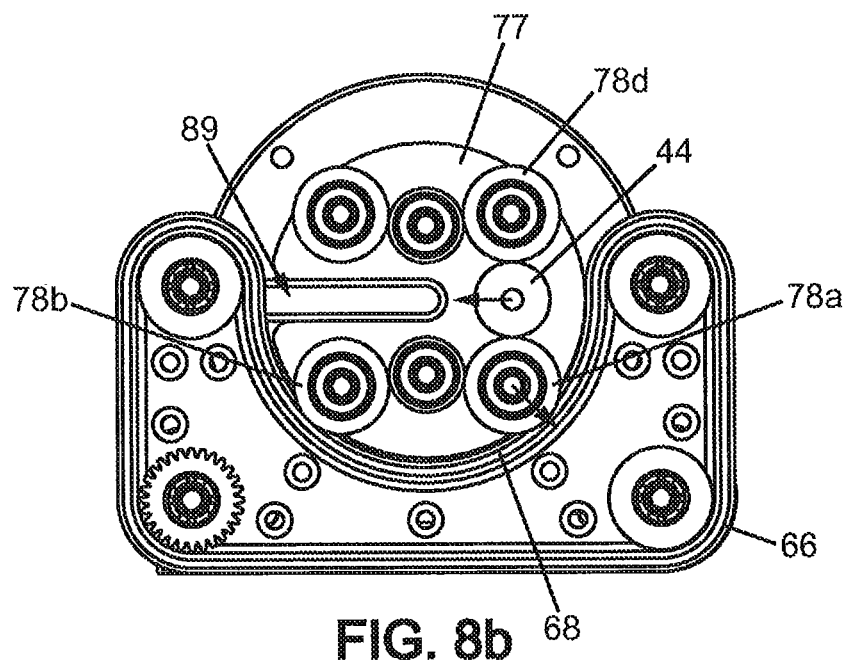
Figure 8C:
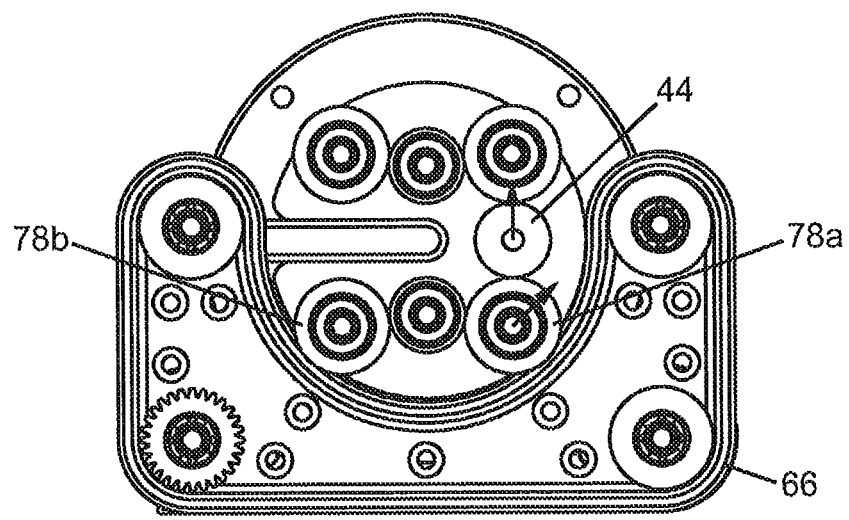

This is particularly visible when one compares FIGS. 8*a* and 8*b*, where arrows have been added to the various moving components to illustrate their relative orientations in the different positions.

Thus, if the operator wants to obtain a pure rotational movement of the elongate flexible medical member 6, the two motors 19 and 20 are controlled at predetermined ratios. During rotation of the mobile unit 22, the elongate flexible medical member 6 remains captured between belts 50 and 51 from which it receives the rotational motion imparted to the mobile unit 22.

Of course, simultaneous translation and rotation of the elongate flexible medical member 6 could be ordered, in which case only the rotation motor 19 may be controlled, or the two motors 19 and 20 may be controlled according to a ratio other than the predetermined ratio in order to achieve rotation only.

As can be seen in FIG. 8*b*, in this position it is not possible to withdraw the elongate flexible medical member 6 via the access opening 89, because the opening is obstructed by the belt 66 of the fixed part. However, there is only one access opening 89. To remove the elongate flexible medical member 6 from the module when in this position, the rotation motor 19 is controlled to achieve rotational movement in the appropriate direction, for example towards the position of FIG. 8*a*. If it is desired to withdraw the elongate flexible medical member 6 from the module with no translational movement of the member within the patient 1, the translation motor 20 is also controlled according to the predetermined ratio in order to generate pure rotational movement.

If, in the position of FIG. 8*b*, translation of the elongate flexible medical member 6 is desired, the rotation driving motor 19 is locked and the translation driving motor is controlled as explained above. In the position represented, the arc portion 68 of the belt 66 causes rotation of gear 78*a* and gear 78*b*, but no longer that of gear 78*d* as above. Regardless of the relative orientation of the mobile unit 22 and the base 21, at least one gear 78*a-d* is in a driving relation with the arc portion 68 of the belt 66. This property defines the minimum central angle of the arc portion 68 of the belt 66, based on the number and arrangement of gears 78*a*-78*d*. In the square configuration shown, the minimum central angle of the arc portion 68 of the belt 66 is at least 90°. In the example presented, 180° is used for clarity.

The structure and operation of the adjustment device according to various embodiments of the invention will now be described in greater detail, with reference to FIG. 9 and subsequent figures.

As shown above, the mobile unit 22 of the drive module 13 is equipped in the embodiment illustrated in FIGS. 2 to 6 with an adjustment device comprising two push elements 56 and 59 that are movable relative to the receiving area E in the lateral adjustment direction Y and each having a push surface 57, 60 engaging with the associated belt 50, 51 so as to move the driving surface 49*b*, 49*b*' thereof along the adjustment direction Y.

One object of the invention is for a practitioner 2 positioned in a room not exposed to x-ray irradiation to be able to control remotely the movement of these push elements 56 and 59 in the lateral adjustment direction Y, regardless of the relative orientation of the mobile unit 22 and of the base 21 relative to the axis of rotation 23. The problem to be solved here is that the push elements 56 and 59 are carried by the mobile unit 22, which is mounted so as to rotate relative to the base 21 about axis 23, and that their movement must be initiated from a control part carried by the base 21 and adapted to receive the motive power required for such movements.

To this end, the invention proposes that the adjustment device 55 comprise a motive power transfer system comprising a control part carried by the base 21, adapted to receive motive power from a motive power source integral to the base 21, and capable of selectively assuming an active adjustment configuration and an inactive configuration, and a transmission part carried by the mobile unit 22, engaging with the control part in the active adjustment configuration, and adapted to convert the motive power into a driving force and to transfer this driving force to the associated push element in order to move it in the lateral adjustment direction Y, the transfer system being adapted to transfer the driving force to the associated push element regardless of the relative orientation of the mobile unit 22 and the base 21 about the axis of rotation 23, when the control part is in the active adjustment configuration.

Figure 9:
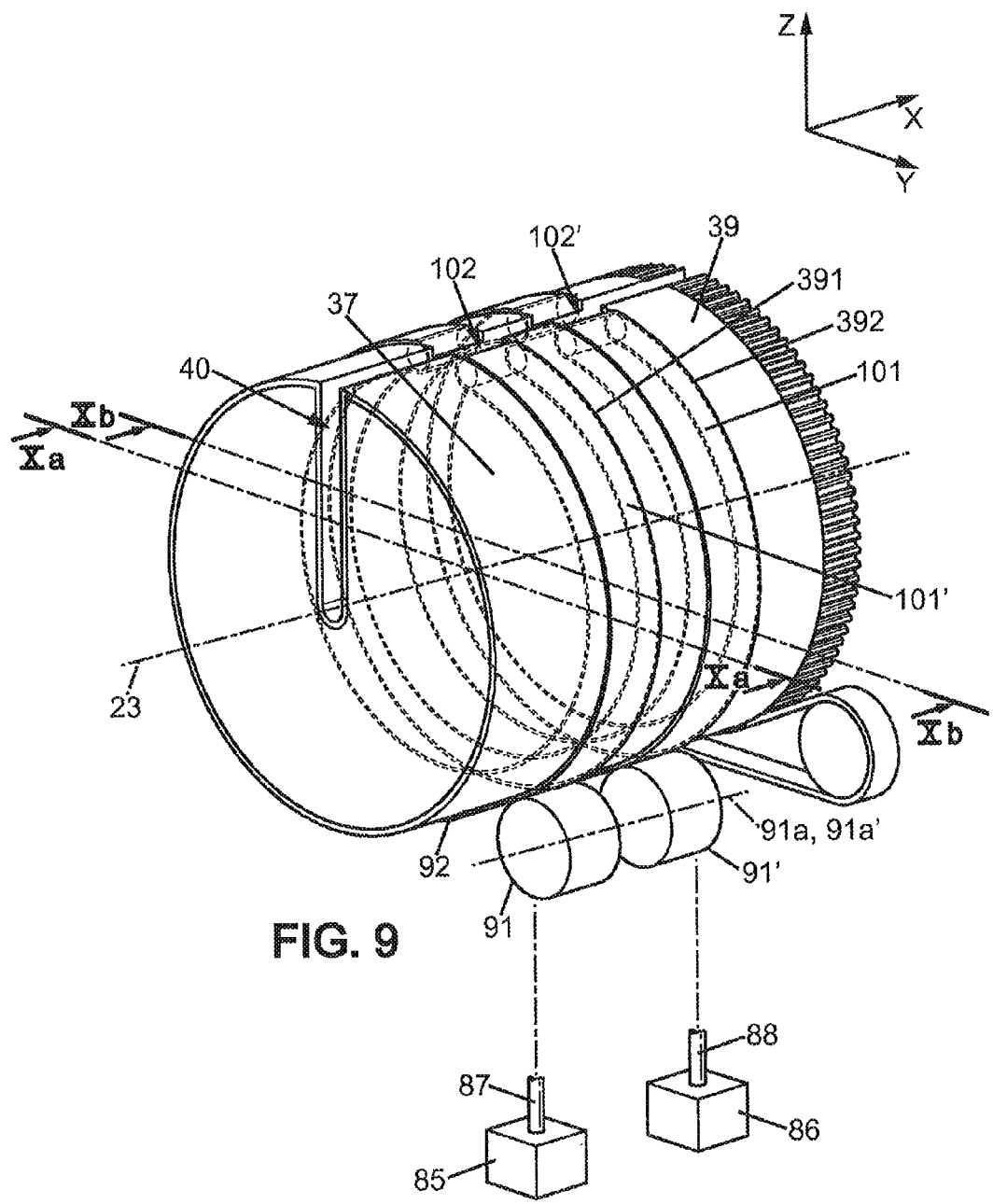
FIG. 9 is a partial perspective view of a drive module equipped with an adjustment device according to a first embodiment of the invention.

FIGS. 9, 10a and 10b illustrate a first embodiment of motive power transfer systems equipping an adjustment device 55 that is part of the drive module.

For clarity, the transfer system 63 described above is not represented in this FIG. 9.

In this embodiment, a first external servomotor 85 and a second external servomotor 86 are utilized, external meaning they are not embedded in the mobile unit 22, and fixed relative to the base 21, similarly to the rotation 19 and translation 20 motors described above in connection with FIG. 2.

These servomotors 85 and 86 are independently controllable by the computerized unit 3 and allow generating motive power in mechanical form, for example torque, which must be converted into a driving force to be transferred to the push elements 56, 59 so that they are moved along the adjustment direction Y.

The receptacle 25 described in connection with figure also comprises two passages (not shown) which can respectively be traversed by a first adjustment shaft 87 and second adjustment shaft 88, respectively connected to the first servomotor 85 and the second servomotor 86.

In this first embodiment illustrated in FIGS. 9, 10a, and 10b, the adjustment device 55 comprises two push elements 56 and 59 movable along the adjustment direction Y and cooperating with an associated belt 50, 51 to move the driving surfaces 49b, 49b' thereof in said adjustment direction Y.

The adjustment device according to FIG. 9 comprises two motive power transfer systems, each of the motive power transfer systems being associated with a respective push element 56, 59.

As the two transfer systems are similar, the following description which references the first transfer system also applies to the second transfer system, similar elements being designated by the same references but accompanied by a ' symbol.

The first transfer system, associated with the first push element 56, comprises a first control part carried by the base 21, adapted to receive motive power from the first servomotor 85 integral to the base 21. The second transfer system, associated with the second push element 59, comprises a second control part carried by the base 21 and adapted to receive motive power from the second servomotor integral to the base 21. The first control part and second control part can selectively adopt an active adjustment configuration and an inactive configuration as will be detailed below.

In particular, according to this first embodiment, the first control part comprises first and second rotary control members 91 and 92 such as pinions/gears or drive rollers, mounted on the base 21 so as to rotate about a respective axis 91a and 92a extending in the main direction X.

A mechanical transfer system (not represented) is provided for operatively connecting the rotary control members 91 and 92 to the first servomotor 85 such that the rotary members 91 and 92 rotate in the same direction about their respective axes 91a, 92a when driven by the first servomotor 85. This transfer system may, for example, make use of a set of bevel gear teeth such as those connecting the rotation 19 and translation 20 motors to the rotation control system 29 and to the translation control system, or a belt system similar to that implemented in the rotation control system 29 for controlling rotation of the mobile unit 22 relative to the base 21 described above and allowing the transfer of rotational movement received by one of the rotary control members 91, adapted to be connected to the shaft 87 of the first servomotor 85, to the other of the rotary control members.

Alternatively, it may be provided that each rotary control member 91, 92 is associated with a dedicated servomotor, the servomotors associated with each of the rotary control members being controlled in a synchronized manner.

In addition, it is arranged that the rotary control members 91, 92, which are in the form of drive rollers or pinions in the embodiment of FIG. 9, can be selectively coupled and uncoupled from the first servomotor 85 to allow transition from an active adjustment configuration in which they are coupled to the first servomotor to drive their rotation, to an inactive configuration in which they are uncoupled from the first servomotor and turn freely on their axis of rotation 91a, 92a. A reversible coupling system known to those skilled in the art may thus be provided between the shaft 87 of the first servomotor 85 and the driving pinions 91 and 92.

Additionally or alternatively, the servomotor 85 can be placed in a freewheeling state, meaning in a state where the motor does not drive the rotary control members 91, 92 and does not oppose or offers very low resistance to the free rotation of these rotary control members 91, 92. In this embodiment, the rotary control members 91, 92 are therefore permanently coupled to the servomotor 85, and the transition of the rotary control members 91, 92 from the active adjustment configuration to the inactive configuration is caused by the change of the servomotor from an active driving state to a freewheeling state.

According to another embodiment, the rotary control members 91, 92 that are parts of the control part may be movable, relative to the transmission part of the motive power transfer system, between a first position corresponding to the active configuration of the control part, where said rotary control members 91 and 92 engage with the transmission part, and a second position corresponding to the inactive configuration of the control part, where said rotary control members 91 and 92 do not engage with the transmission part and are spaced apart from it. In particular, to change from the active adjustment configuration to the inactive configuration, these rotary control members 91 and 92 can be moved in the main direction X and/or in the lateral direction Y and/or in the transverse direction Z by means of a dedicated movement device (not shown), until they are distanced from the transmission part and no longer engage with it.

This prevents the rotary control members 91, 92, when in the inactive configuration, from causing unintentional movement of the associated push element 56 during rotation of the mobile unit 22 relative to the base 21 about the axis 23, which would have a detrimental effect on the clamping and/or movement of the flexible medical member 6.

As shown in FIG. 9, the transmission part of each of the motive power transfer systems comprises a circular element 101, 101' carried by the mobile unit 22 and centered on the axis of rotation 23.

As can be seen more clearly in FIGS. 10*a* and 10*b*, the circular element 101, 101' has a radially outer side 101*a*, 101*a*' which cooperates with the rotary control members 91, 91', 92, 92' that are parts of the associated control part, and a radially inner side 101*b*, 101*b*' which engages with a transmission mechanism that is part of the associated transmission part and is described in greater detail below.

Furthermore, in this embodiment illustrated in FIG. 9, the housing 39 has an access opening 40 which provides access on the one hand to the receiving space E of the elongate flexible medical member 6 and on the other hand to outside the mobile unit 22 in the radial direction. This access opening 40 should be always be radially accessible to allow easy removal of an elongate flexible medical member 6 from the receiving space E inside the drive module regardless of the relative orientation of the mobile unit 22 and the base 21 about axis 23, as was described above in connection with FIGS. 2, 7, and 8*a* to 8*c*.

To allow such easy removal of the elongate flexible medical member 6 from the drive module, the adjustment device 55 for the push elements 56, 59 should not radially block the access opening 40 of the housing 39, regardless of the adjustment position of each of the push elements 56, 59 along the adjustment direction Y.

Also, in the first embodiment of the invention visible in FIGS. 9, 10*a*, and 10*b*, the circular element 101, 101' that is part of the transmission part of each of the motive power transfer systems has an opening 102, 102' extending along the entire length of the circular element 101, 101' in the main direction X and radially aligned with the access opening 40 of the housing 39 regardless of the adjustment position of each of the push elements 56, 59 along the adjustment direction Y.

More specifically, in the first embodiment of the invention shown in FIGS. 9, 10*a*, and 10*b*, the circular element that is part of the transmission part of each of the transfer systems consists of a continuous flexible belt 101, 101' following a generally C-shaped path. The path of each belt is centered on the axis of rotation 23 of the mobile unit 22 relative to the base 21; this path, in other words the route followed by each belt, is stationary, fixed relative to the mobile unit about the axis of rotation 23.

The circumferential dimension of the opening 102, 102' of the C defined by the path of each belt 101, 101' is at least equal to that of the access opening 40. This ensures that the access opening 40 is not obstructed, or rendered radially inaccessible, by an element of the adjustment device 55.

The presence of this opening 102, 102' in the path of each belt 101, 101' requires providing a plurality of control members 91, 92, here two such members for each belt, spaced sufficiently apart from each other along the circumference to ensure that at least one of these control members 91, 92, when they are in the active adjustment configuration, engages with the outer face of the belt regardless of the relative orientation of the mobile unit 22 and the base 21 about the axis of rotation 23. As the belts 101, 101' are supported in a stationary path by the mobile unit 22, when this mobile unit 22 rotates relative to the base 21 about the axis 23, the belts 101, 101' are rotated along with it. During this rotation, when the opening 102, 102' of each belt 101, 101' reaches a first control member 91, 91', the first control member 91, 91' is no longer in contact with the outer surface of the associated belt 101, 101' and can no longer advance this belt along its path. This is why a second control member 92, 92' is provided: to take over for the first control member 91, 91' in driving the belt 101, 101' along its path when the first control member 91, 91' is opposite the opening 102, 102' of the belt 101, 101', and vice versa.

In other words, the spacing between the two control members 91, 91' and 92, 92' along the periphery is chosen so as to be greater than the circumferential dimension of the opening 102, 102' of the associated belt 101, 101' such that at least one of said control members 91, 91' and 92, 92' is in contact with the associated belt regardless of the orientation of the mobile unit 22 relative to the base 21 about the axis of rotation 23, when the control members 91, 91' and 92, 92' are in the active adjustment configuration.

As is particularly visible in FIGS. 9, 10*a*, and 10*b*, each flexible belt 101, 101' is received in a respective annular channel 391, 392 provided on the outer face of the housing 39, between the first and second ends 36*a*, 36*b* of the housing 39 along the main direction X. Each belt 101, 101' is guided in its movement along its path by the bottom and sides of the associated annular channel 391, 392, and by two idler guide rollers 104, 105, 104', 105' removably mounted on the housing 39 (for assembling the belt 101, 101' on the housing 39) near the access opening 40.

Each flexible belt 101, 101' has a radially outer side 101*a*, 101*a*' forming the "outer face" of the circular element, engaging with the associated rotary control members 91, 92, 91', 92' when they are in the active adjustment configuration, and a radially inner side 101*b*, 101*b*' forming the "inner face" of the circular element, cooperating with an associated transmission mechanism.

We will now describe a first transmission mechanism that is part of the first transmission part associated with the first push element 56, with reference to FIG. 10*a*.

As can be seen in FIG. 10*a*, the frame 43 that is part of the mounting integral with the mobile unit 22 supports a first rotary transfer member 106 mounted in the frame 43 so as to rotate freely about an axis extending in the main direction X. The housing 39 is provided with a window 393 to the space inside the housing 39, at the first rotary transfer member 106 mounted on the frame 43, said window also opening onto the channel 391 that receives the belt 101. The first rotary transfer member 106 can thus engage with the radially inner side 101*b* of the belt 101 so that movement of the belt 101 along its path causes rotation of the rotary transfer member 106.

The transmission mechanism that is part of the first transmission part associated with the first push element 56 further comprises a worm gear 107 rotatably supported on the frame 43 and extending in the lateral direction Y. This worm gear 107 engages with the rotary transfer member 106 such that rotation of said rotary transfer member 106 about its axis of rotation causes rotation of the worm gear 107 about its axis of rotation. The push element 56 associated with this first transmission mechanism also has a threaded portion 561 engaging with the worm gear 107 so that rotation of the worm gear 107 about its axis causes linear movement of the push element 56 along this same axis extending in the lateral adjustment direction Y. The position of the first push element 56 is thus adjusted in the lateral adjustment direction Y.

In FIG. 10b, a second transmission mechanism that is part of the second transmission part associated with the second push element 59 is represented.

As can be seen in this FIG. 10b, the second transmission mechanism has a structure that is substantially symmetrical to that of the first transmission mechanism. Thus, the frame 43 supports a second rotary transfer member 106' mounted so as to rotate freely in the frame 43 about an axis extending in the main direction X, the housing 39 is provided with a window 393' to the space inside the housing 39, at the second rotary transfer member 106' mounted on the frame 43, said window also opening onto the channel 392 that receives the belt 101'. The second rotary transfer member 106' can thus engage with the radially inner side 101b' of the belt 101' so that movement of the belt 101' along its path causes rotation of the rotary transfer member 106'.

The transmission mechanism that is part of the second transmission part associated with the second push element 59 further comprises a worm gear 107' rotatably supported on the frame 43 and extending in the lateral direction Y. This worm gear 107' engages with the rotary transfer member 106' such that rotation of said rotary transfer member 106' about its axis of rotation causes rotation of the worm gear 107' about its axis of rotation. The push element 59 associated with this second transmission mechanism also has a threaded portion 561' engaging with the worm gear 107' so that rotation of the worm gear 107' about its axis causes linear movement of the push element 59 along this same axis extending in the lateral adjustment direction Y. The position of the second push element 59 is thus adjusted in the lateral adjustment direction Y.

In this embodiment, one can see that the first and second push elements 56 and 59 can be moved independently along the lateral adjustment direction Y, which allows adjusting the spacing between the driving surfaces 49b, 49b' of the belts 50, 51 to adapt to different diameters of flexible medical member 6 to be driven, and adjusting the offset between the axis of rotation 23 and the axis along which the elongate flexible medical member 6 extends between the driving surfaces 49b, 49b' of the belts 50, 51, to facilitate driving the rotation of said member 6 about axis 23 (lever arm effect).

We will now describe a second embodiment of motive power transfer systems equipping an adjustment device 55 that is part of the drive module, with reference to FIGS. 11, 12a to 12d, and 13.

In this second embodiment, only the transmission parts associated with each of the motive power transfer systems differ from the first embodiment described above, and these will therefore be described in detail below; the other elements remain similar or identical.

Figure 11:
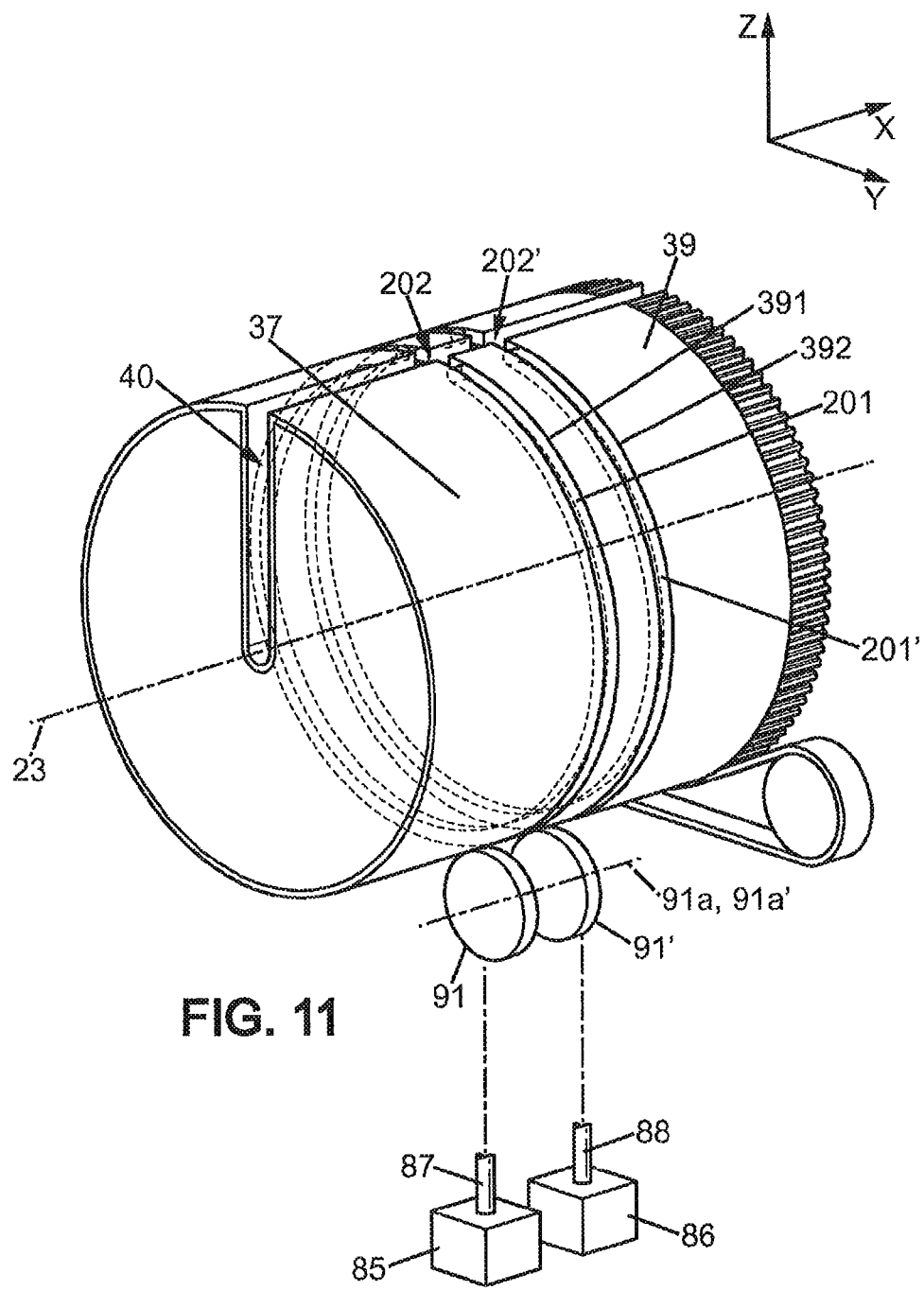
FIG. 11 is a partial perspective view of a drive module equipped with an adjustment device according to a second embodiment of the invention.

Referring to FIG. 11, in this second embodiment the housing 39 has two channels 391, 392 on its outer peripheral surface 37, each designed to accommodate a circular element in the form of a ring 201, 201' that is part of an associated transmission part. These rings may be slightly flexible so that they can be slightly deformed for threading onto the outer surface 37 of the housing 39 at one of its ends 36a, 36b along the main direction X, and sliding on this outer surface 37 along the main direction X until they reach their intended channels 391, 392 where they fit into place within these grooves by elastic recovery.

In this second embodiment, the rings 201, 201' are rotatable relative to the housing 39 of the mobile unit 22, about the axis of rotation 23. As can be seen in FIG. 11, the rotation of each ring 201, 201' relative to the housing 39 about the axis of rotation 23 is induced by the engaging of each ring 201, 201' with two rotary control members 91, 92, 91', 92' which, in the active adjustment configuration, engage with the radially outer faces 201a, 201a' of the rings 201, 201'.

In the manner described with reference to the first embodiment illustrated in FIGS. 9, 10a, and 10b, the rotary control members 91, 92, 91', 92' associated with each of the rings 201, 201' can transition from the active adjustment configuration to the inactive configuration either by being uncoupled from their respective servomotor 85, 86, or by being moved away from the associated ring 201, 201' until they are distanced from it.

In this second embodiment, the rings 201, 201' that are part of the associated transmission parts have an opening 202, 202' whose circumferential dimension is chosen so that the access opening 40 of the mobile unit 22 is always radially unobstructed/accessible, regardless of the relative position of the rings 201, 201' with respect to the housing 39 of the mobile unit 22 about the axis of rotation 23, their relative positions being directly dependent on the positions of the push elements 56 and 59 along the adjustment direction as will be discussed below.

The relative rotation of the rings with respect to the mobile unit 22 is limited to an angular range chosen to comply with this principle, while allowing adjustment of both the spacing and the offset of the push elements 56 and 59 to the various settings desired. This limitation on the angular range of the relative rotation between the rings 201, 201' and the housing 39 of the mobile unit 22 may, for example, be achieved by means of stops provided for example in the channels 391 and 392, or directly by the push elements 56 and 59 coming into contact with each other via the belts 50 and 51.

However, as withdrawing the medical member 6 from the mobile unit 22 through the access opening 40 may require at least slightly relaxing the grip on the member 6, the ring controlling the gap between push elements could slightly protrude into the access opening 40 when the member 6 is tightly clamped, and completely unblock the opening when the grip on the member 6 is slightly relaxed.

We will now describe a sequence for adjusting the position of the push elements 56 and 59 in the lateral adjustment direction Y by means of motive power transfer systems implemented according to the second embodiment of the invention, with reference to FIGS. 12a to 12c.

These FIGS. 12a to 12c are schematic views showing a frame 43 schematically represented as a block, a first push element 56, a second push element 59, a tensioner 61, a first belt 50 associated with the first push element 56, a second belt 51 associated with the second push element 59 and with the tensioner 61, a first ring 201 and first rotary transfer member 206 that are part of a first transmission mechanism, a second ring 201' and second rotary transfer member 206' that are part of a second transmission mechanism, and an elongate flexible medical member lying within the receiving space E defined in the mobile unit 22 between the belts 50 and 51.

In addition, illustrated with dotted lines in these figures is the portion of the housing 39 of the mobile unit 22 which defines the access opening 40. Lastly, although not shown directly in these figures, the housing 39 of the mobile unit 22 is provided with windows similar to the window 393 of the first embodiment and allowing each of the first and second rotary transfer members 206, 206' to engage with the radially inner surface 201b, 201b' of the associated ring 201, 201'.

Thus, FIG. 12a shows an initial position of the push elements 56 and 59 before adjusting in the adjustment direction Y. In this position, the first and second push elements 56 and 59 are fully apart in the adjustment direction Y. An elongate flexible medical member 6 has been placed in the receiving area E of the mobile unit by insertion for example radially through the access opening 40 of the housing 39 and the openings 202, 202' of the rings 201, 201'.

In this second embodiment, and as will be described in more detail with reference to FIG. 13, the first transmission part associated with the first push element 56 comprises a first transmission mechanism adapted to move the first push element 56 toward the second push element 59 along the adjustment direction Y, so as to adjust the spacing between the belts 50 and 51 to the diameter of the elongate flexible medical member 6 to be driven. In addition, the second transmission part associated with the second push element 59 comprises a second transmission mechanism adapted to move the first push element 56 and second push element 59 jointly along the adjustment direction Y, so as to adjust the offset in the adjustment direction Y between the axis of rotation 23 and the axis X2 along which the elongate flexible medical member 6 extends at the belts 50 and 51.

Thus, starting from the configuration illustrated in FIG. 12a, a practitioner can cause the first ring 201 to rotate by placing the associated rotary control members 91, in the active adjustment configuration. In the manner described with reference to the first embodiment, these rotary control members 91, 92 are spaced sufficiently apart from one another along the circumference to ensure that at least one of them remains in contact with the outer face 201a of the ring 201 regardless of the relative orientation of the mobile unit 22 and the base 21 about the axis of rotation 23. In other words, the central angle of the arc between these rotary control members 91, 92 along the circumference is at least equal to the central angle of the circumferential opening 202 of the ring 201.

Rotation of the first ring 201, for example counterclockwise in FIGS. 12a-12c as indicated by arrow F1 in FIG. 12a, causes the rotation of the first rotary transfer member 206 about its axis extending in the main direction X, and the translational movement in the adjustment direction Y, by means of the first transmission mechanism, of the first push element 56 towards the second push element 59 which is held stationary. As can be seen in FIG. 12b, this phase brings the driving surface 49b of the first belt 50 closer to the driving surface 49b' of the second belt 51 until the elongate flexible medical member 6 is gripped between the belts 50 and 51, for example with a predetermined force adjusted by means of an elastic member (not shown) such as a spring, arranged in a suitable manner between the first push element 56 and a push element support 561 relative to which the push element 56 is movable in the adjustment direction Y against the force exerted by said elastic element, as shown in FIG. 13.

If the practitioner 2 wishes to adjust an offset in the adjustment direction Y between the axis of rotation 23 and the axis X2 along which the elongate flexible medical member 6 extends at the belts 50 and 51, the practitioner can cause rotation of the second ring 201' by placing the associated rotary control members 91', 92' in the active adjustment configuration. In the manner described with reference to the first embodiment, these rotary control members 91', 92' are spaced sufficiently apart from one another along the circumference to ensure that at least one of them remains in contact with the outer face 201a' of the ring 201' regardless of the relative orientation of the mobile unit 22 and the base 21 about the axis of rotation 23.

Rotation of the second ring 201', for example clockwise in FIGS. 12a to 12c as indicated by arrow F2 in FIG. 12b, causes the rotation of the second rotary transfer member 206' about its axis extending in the main direction X and the joint translational movement in the adjustment direction Y, by means of the second transmission mechanism, of the first push element 56 and the second push element 59. This phase allows adjusting the offset in the adjustment direction Y between the axis of rotation 23 and the axis X2 along which the elongate flexible medical member 6 extends at the belts 50 and 51.

Figure 13:
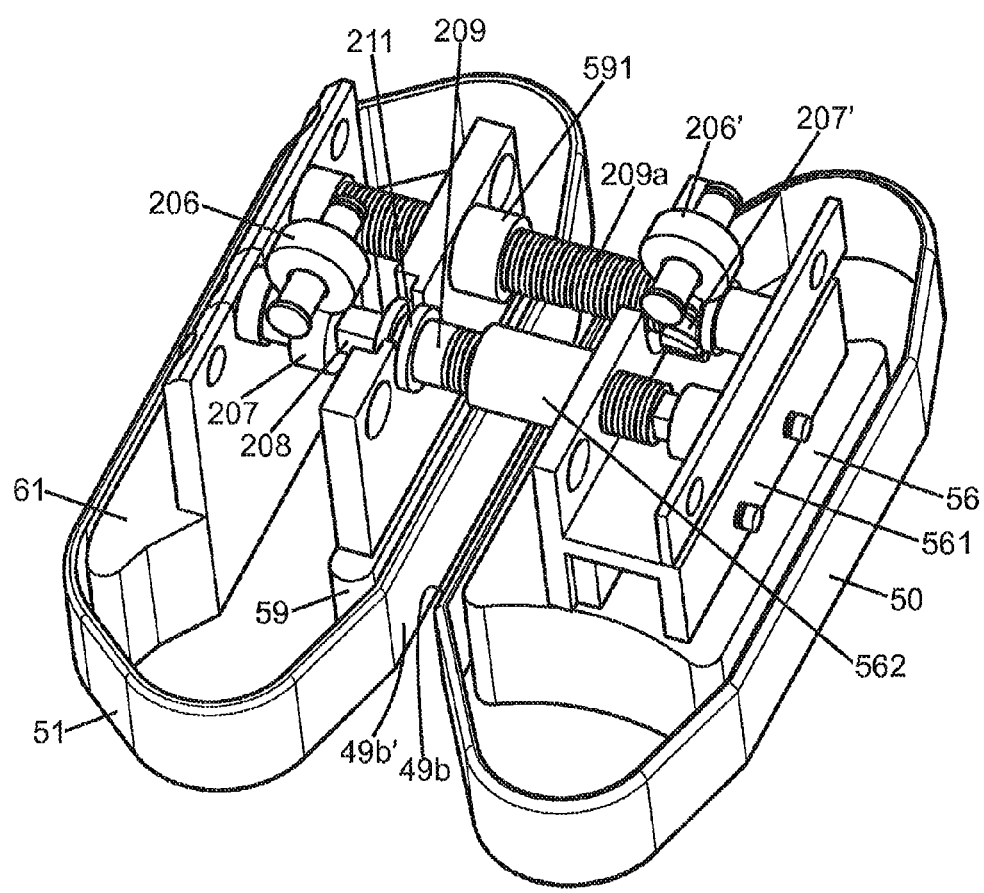
FIG. 13 is a partial perspective view from below, illustrating an adjustment mechanism carried by the mobile unit.

We will now describe the first and second transmission mechanisms according to the second embodiment of the invention, with reference to FIG. 13.

This FIG. 13 shows a bottom view of the first push element 56, the second push element 59, the tensioner 61, the first belt 50 and second belt 51 which can be moved along the adjustment direction Y relative to the mounting 43, as well as the first transmission mechanism and second transmission mechanism.

As can be seen in this FIG. 13 which illustrates non-limiting embodiments of the first and second transmission mechanisms, the first transmission mechanism comprises the first rotary transfer member 206. The first transmission mechanism further comprises a first gear 207, with which the first rotary transfer member 206 is in driving engagement, the first gear 207 being integral with a shaft 208 of non-circular cross-section, for example square, mounted so as to rotate freely about its axis extending in the adjustment direction Y on the mounting 43. The shaft 208 is threaded through an opening of complementary cross-section provided inside a first worm gear 209 extending as an extension of the shaft 208. The first worm gear 209 comprises a grooved ring 211 that fits into a complementary opening provided on the second push element 59. The width of the opening provided on the second push element 59 is adapted to receive the groove of the ring 211, the lateral edges defining the opening being received between the side walls of the groove. This first worm gear 209 can thus rotate freely about its axis relative to the second push element 59 while being guided in rotation on the second push element 59 by the cooperation of the ring 211 and the opening provided on the second push element 59. In addition, the first worm gear 209 is fixed translationally along the adjustment direction Y of the second push element 59, by means of the groove provided on the ring 211.

The first push element 56 is carried by a first push element support 561, with the option of translational motion along the adjustment direction Y against the force exerted by an elastic member (not shown) of the first push element relative to the first push element support 561. The first push element support 561 drives the first push element 56 along the adjustment direction when the first worm gear 209 is rotated by the shaft 208 and first gear 207; for this purpose, the first push element support 561 has a threaded portion 562 engaging with the first worm gear 209.

Thus, when a practitioner 2 causes movement of the first ring 201 by placing the associated rotary control members 91, 92 in the active adjustment configuration, the first ring 201 rotates the first rotary transfer member 206, causing the shaft 208 to rotate by means of the first gear 207. The shaft 208 then rotates the first worm gear 209, causing linear movement along the adjustment direction Y of the first push element support 561 and of the first push element 56 towards the second push element 59. The spacing between push elements 56 and 59 is thus adjusted, which adjusts the spacing between the driving surfaces 49b and 49b' of the belts 50 and 50 in the adjustment direction Y.

Still in relation to this FIG. 13, the second transmission mechanism comprises the second rotary transfer member 206'. The second transmission mechanism further comprises a second gear 207', with which the second rotary transfer member 206' is in driving engagement, the second gear 207' being integral with a second worm gear 209' extending parallel to the first worm gear 209, meaning along the adjustment direction Y. The second push element 59 has a threaded portion 591 engaging with the second worm gear 209' such that rotation of the second worm gear 209' causes translational movement of the second push element 59 along the adjustment direction.

Thus, when a practitioner 2 causes movement of the second ring 201' by placing the associated rotary control members 91', 92' in the active adjustment configuration, the second ring 201' rotates the second rotary transfer member 206', causing the second worm gear 209' to rotate by means of the second gear 207', resulting in translational movement along the adjustment direction Y of the second push element jointly with the first push element support 561, the latter being translationally integral, along the adjustment direction, with the second push element 59 due to the threaded portion 562 engaging with the first worm gear 209 and grooved ring 211, guided by the shaft of non-circular cross-section 208. Adjustment of the offset along the adjustment direction Y between the axis of rotation 23 and the axis X2 along which the elongate flexible medical member extends at the belts 50 and 51 is thus achieved, by jointly moving the first and second push elements 56 and 59 along the adjustment direction.

Figure 14:
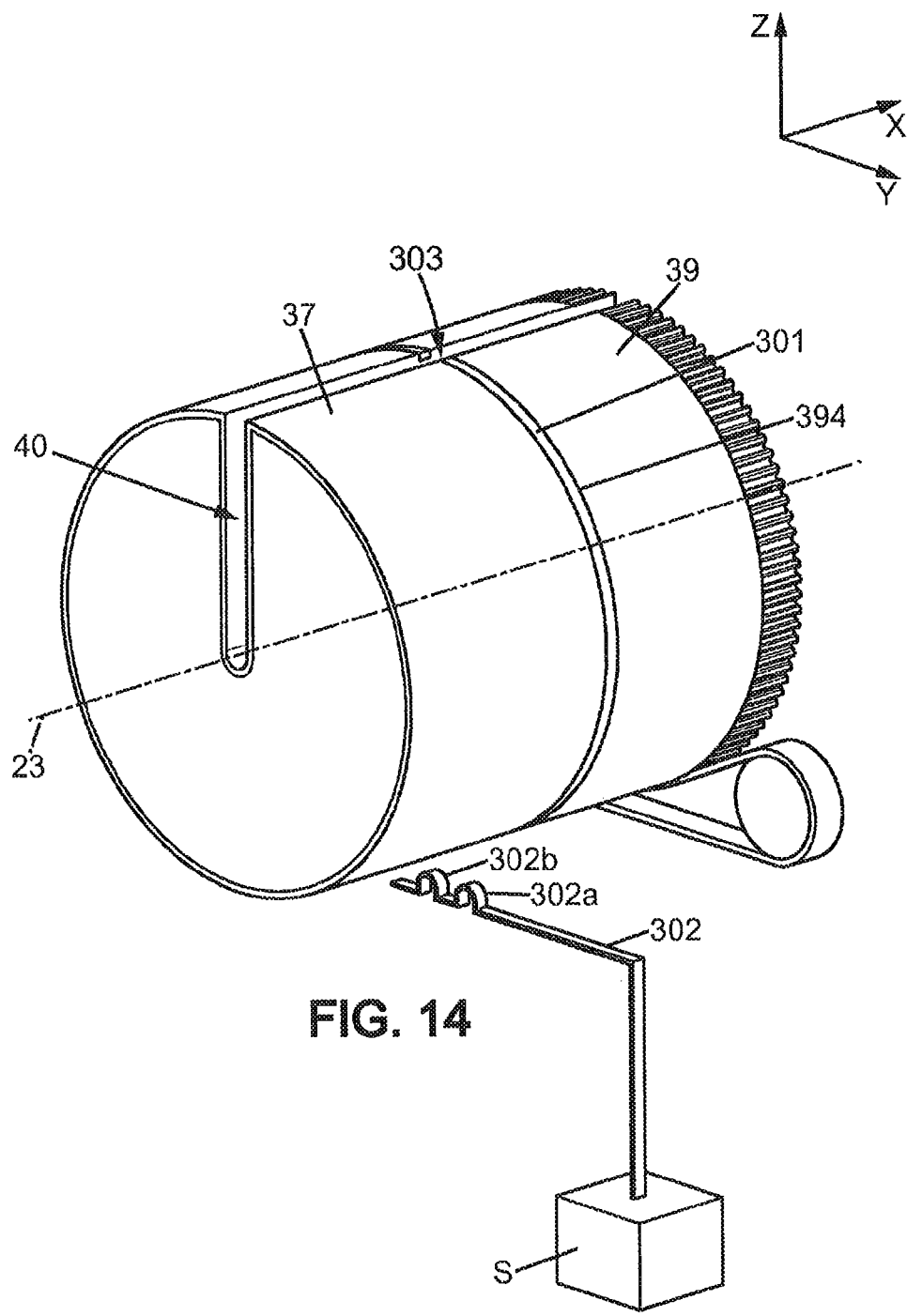
FIG. 14 is a partial perspective view of a drive module equipped with an adjustment device according to a third embodiment of the invention.
Figure 15:
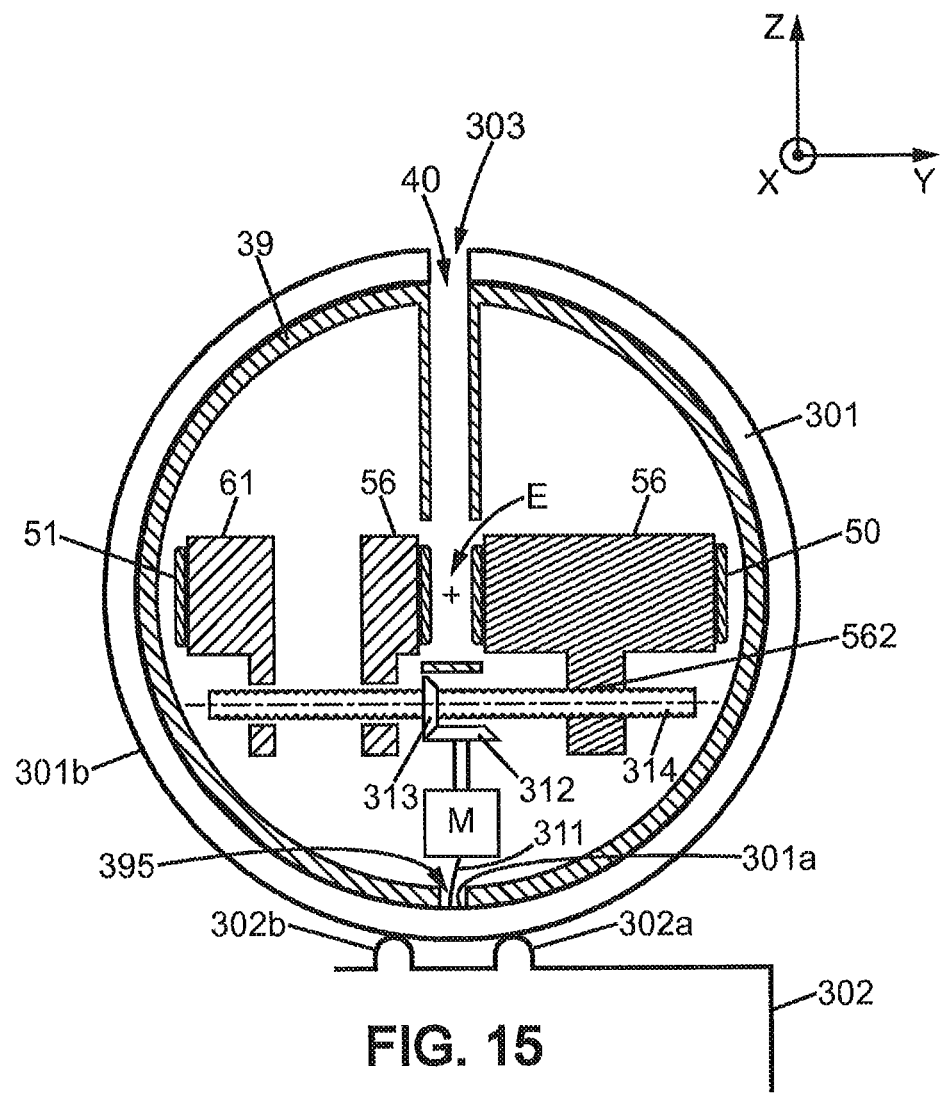
FIG. 15 shows a section view along line XV of the drive module of FIG. 14.

We will now describe a third embodiment of a motive power transfer system according to the invention, with reference to FIGS. 14 and 15.

In this embodiment, the adjustment device comprises two push elements 56 and 59 and a single motive power transfer system for both push elements 56 and 59.

As can be seen in FIG. 15, in this third embodiment the mobile unit 22 has an embedded motor M that is part of the transmission mechanism of the transmission part, for example carried by the mounting 43. The problem here lies in bringing the motive power, in the form of electricity, from a power source S integral to the base 21 to the motor M embedded in a mobile unit 22 that is rotatable relative to the base 21 about the axis of rotation 23, and achieving this regardless of the relative orientation of the mobile unit 22 and the base 21 about the axis 23.

According to this third embodiment of the invention, this is done by utilizing a slip ring comprising a first portion 302 that is part of the control part carried by the base 21 and connected to an electrical power source S integral with the base 21, and a second portion 301 that is part of the transmission part and connected to the motor M embedded in the mounting 43 of the mobile unit 22.

The first slip ring portion 302 is movable on the base 21 relative to the transmission part, between a first position corresponding to the active adjustment configuration in which the first slip ring portion 302 engages with the second slip ring portion 301 that is part of the transmission part and connected to the motor M embedded in the mounting 43 of the mobile unit 22, for example via one or more connecting wires 311, and a second position corresponding to the inactive configuration in which the first slip ring portion 302 does not engage with, is apart from, the second slip ring portion 301, as shown in FIG. 14.

Additionally or alternatively, it could be arranged that the transition from the active adjustment configuration to the inactive configuration is achieved by opening a switch arranged between the first slip ring portion 301 and the electrical power source S.

In this third embodiment of the invention, the transmission part of the motive power transfer system comprises a second slip ring portion in the form of a ring 301 fixedly received in a channel 394 provided on the peripheral surface 37 of the housing 39. This ring may be slightly flexible so that it can be slightly deformed for threading onto the outer surface 37 of the housing 39 at one of its ends 36a, 36b along the main direction X, and sliding on this outer surface 37 along the main direction X until it reaches the intended channel 394 where it fits into place within the groove by elastic recovery.

As can be seen in FIGS. 14 and 15, the ring 301 has an opening 303 whose circumferential dimension is at least equal to that of the opening 40 of the housing 39.

The control part of the motive power transfer mechanism according to this third embodiment comprises the first slip ring portion 302 which, when in the active adjustment configuration, is maintained in sliding contact with the outer surface 301b of the second slip ring portion 301 integral with the mobile unit 22. For this purpose, and similarly to what has been described for the rotary control members of the first and second embodiments, the first slip ring portion 302 has two control members 302a, 302b spaced apart along the circumference by a distance at least equal to the size of the opening 303 of the ring 301, to ensure that when the first slip ring portion 302 is in the active adjustment configuration, at least one of the members 302a, 302b remains in contact with the outer surface 301b of the slip ring 301 regardless of the relative orientation of the mobile unit 22 and the base 21 about the axis of rotation 23.

In addition, the housing 39 has a window 395 which allows connecting the embedded motor M to the inner surface 301a of the ring 301 via one or more connecting wires 311.

Thus, in this third embodiment of the invention, starting from the configuration shown in FIG. 14, when a practitioner 2 wishes to clamp the flexible medical member between the belts 50, 51 by moving the push elements 56, 59, he or she first causes the first slip ring portion 302 to transition to the active configuration. In the current case, the practitioner causes the first slip ring portion 302 to move so that its control members 302a, 302b come in contact with the slip ring 301. Once this contact is established, the motive power in the form of electrical power coming from the electrical power source S, and possibly other control signals, are transmitted to the embedded motor M via the connecting wires 311 in continuous contact with the slip ring 301 regardless of the relative orientation of the mobile unit 22 and the base 21.

Referring to FIG. 15, in this third embodiment of the invention, the transmission part of the motive power transfer system when in the active adjustment configuration as illustrated in FIG. 15, is adapted to move, during a first portion of the actuating stroke, the first push element 56 towards the second push element 59 in order to adjust the spacing between the driving surfaces 49b, 49b' of each of the belts 50 and 51 along the adjustment direction Y, and to move jointly, during a second portion of the actuating stroke which follows the first portion, the first and second push elements 56, 59 along the adjustment direction Y in order to adjust the offset between the axis of rotation 23 of the mobile unit 22 relative to the base 21 and the axis along which the elongate flexible medical member 6 extends between the belts 50 and 51.

Thus, and as can be seen schematically in FIG. 15, the transmission part of the motive power transfer system according to the third embodiment of the invention comprises, in addition to the embedded motor M, wires 311, and slip ring 301, a rotary transfer member 312 provided at the output shaft of the embedded motor M and engaging with a gear 313 integral with a worm gear 314 extending in the adjustment direction Y. The first push element 56 is provided with a threaded portion 562 engaging with the worm gear 314 such that rotation of the worm gear about its axis extending in the adjustment direction Y causes translational movement of the first push element 56 along this adjustment direction Y.

Thus, when the embedded motor M is supplied with power, it rotates the rotary transfer member 312 which causes the worm gear 314 to rotate about its axis. In this first actuating stroke, the first push element 56 is moved toward the second push element 59 by the engagement of the threaded portion 562 with the worm gear 314, until the elongate flexible medical 6 is gripped between the belts 50, 51. The spacing between the belts 50, 51 is thus adjusted to the diameter of the elongate flexible medical member 6 to be driven, thus clamping this member 6, for example with a predetermined force calibrated by means of an elastic member such as a spring (not shown) extending in the adjustment direction Y between the second push element 59 and the tensioner 61.

Then, while continuing the rotation of the embedded motor in the same direction of rotation, in a second portion of the actuating stroke which follows the first, the first push element 56 is driven translationally along the adjustment direction Y, in the same direction as during the first actuating stroke, and pushes against the second push element 59 through the belts 50, 51 and the elongate flexible medical member 6 gripped between these belts 50, 51, which causes the joint movement of the second push element 59 along the adjustment direction Y so as to adjust the offset between the axis of rotation 23 of the mobile unit 22 relative to the base 21 and the axis along which the elongate flexible member medical 6 extends between the belts 50 and 51.

Throughout the above description of the invention, the driving engagement of rotary members having respective perpendicular axes of rotation may be achieved by means of drive transfer elements known to the skilled person, in particular right-angle elements, such as bevel gears, tapered friction rollers, or other such elements.

Furthermore, the engaging contact surfaces driving these various rotary members may be provided with corresponding teeth and/or coatings suitable for facilitating the driving engagement of these rotary elements.

The invention claimed is:

1. A module for driving a robotic catheterization system, comprising a base and a mobile unit mounted so as to relative to the base about an axis of rotation extending along a main direction, the mobile unit comprising:
   a mounting in which is defined a receiving space extending along the main direction and adapted to receive an elongate flexible medical member;
   a translation driving means, carried by the mounting and comprising a drive element having a driving surface adapted to engage with the flexible medical member so as to generate a translational movement of said medical device along the main direction;
   said drive module further comprising an adjustment device comprising:
   a push element that is part of the mobile unit, movable relative to the receiving space along a lateral adjustment direction perpendicular to the main direction and having a push surface engaging with the drive element so as to move the driving surface along the adjustment direction;
   a motive power transfer system comprising a control part carried by the base, adapted to receive motive power from a motive power source integral with the base, and capable of selectively adopting an active adjustment configuration and an inactive configuration, and a transmission part carried by the mobile unit, engaging with the control part in the active adjustment configuration and adapted to convert the motive power into driving force and to transfer said driving force to the push element in order to move said push element along the adjustment direction,
   and wherein the motive power transfer system is adapted to transfer the driving force to the push element regardless of the relative orientation of the mobile unit and the base about the axis of rotation, when the control part is in the active adjustment configuration.

2. The drive module according to claim 1, wherein the control part is adapted to be selectively coupled to and uncoupled from the motive power source in order to switch from the active adjustment configuration to the inactive configuration.

3. The drive module according to claim 1, wherein the control part is movable relative to the transmission part, between a first position corresponding to the active adjustment configuration, in which the control part engages with the transmission part, and a second position corresponding to the inactive configuration, in which the control part does not engage with the transmission part.

4. The drive module according to claim 1, wherein the mobile unit is mounted so as to rotate relative to the base about a first axis of rotation, and wherein the receiving space comprises a defined portion at the mounting along a second axis, parallel to the first axis and offset relative thereto, and wherein the adjustment device is adapted to adjust the offset of the first and second axis.

5. The drive module according to claim 4, wherein the translation driving means comprises a first drive element and a facing second drive element, the receiving space extending between said drive elements, each drive element having a driving surface adapted to engage with the flexible medical member,
   and wherein the adjustment device comprises a first push element and a second push element, each part of the mobile unit and each movable relative to the receiving space along the adjustment direction, each push element having a push surface engaging with an associated drive element so as to move the driving surface of said drive element along the adjustment direction.

6. The drive module according to claim 5, wherein the adjustment device comprises a first motive power transfer system and a second motive power transfer system which are associated with each of the push elements.

7. The drive module according to claim 6, wherein, when the control part of the first motive power transfer system is in the active adjustment configuration, the transmission part of the first motive power transfer system is adapted to move the first push element towards the second push element so as to adjust the spacing between the driving surfaces of each of the drive elements along the adjustment direction,
   and wherein, when the control part of the second motive power transfer system is in the active adjustment configuration, the transmission part of the second motive power transfer system is adapted to move the first and second push elements jointly along the adjustment direction in a manner that adjusts the offset of the first axis (23) and second axis.

8. The drive module according to claim 5, wherein the adjustment device comprises a single motive power transfer system for the two push elements, and wherein, when the control part of said motive power transfer system is in the active adjustment configuration, the transmission part of said motive power transfer system is adapted to, during a first portion of the actuating stroke, move the first push element towards the second push element so as to adjust the spacing between the driving surfaces of each of the drive elements along the adjustment direction, and, during a second portion of the actuating stroke which follows the first portion, to move the first and second push elements jointly along the adjustment direction in a manner that adjusts the offset of the first axis and second axis.

9. The drive module according to claim 1, wherein the transmission part comprises a circular element centered on the axis of rotation of the mobile unit relative to the base and having a radially outer side which engages with the control part in the active adjustment configuration, and a radially inner side, the transmission part further comprising a transmission mechanism engaging with the inner side of the circular element.

10. The drive module according to claim 9, wherein the mounting of the mobile unit extends between first and second ends along the main direction and has an access opening extending between the first and second ends along the main direction, opening on the one hand to the receiving space defined in the mounting and on the other hand to outside the mobile unit in the radial direction, and wherein the circular element of the transmission part has an opening extending for the entire length of the circular element along the main direction, at least a portion of the opening of the circular element being radially aligned with the access opening of the mounting regardless of the position of the push element in the adjustment direction, allowing access to the receiving space of the mounting from outside the mobile unit.

11. The drive module according to claim 10, wherein the control part comprises a plurality of control members of which at least one engages in the active adjustment configuration with the outer side of the circular element that is part of the transmission part, regardless of the relative orientation of the mobile unit and the base about the axis of rotation.

12. The drive module according to of claim 10, wherein the control part comprises a rotary control member which, in the active adjustment configuration, is in a driving relation with the outer side of the circular element.

13. The drive module according to claim 12, wherein the circular element consists of a ring or a belt mounted so as to rotate on the mobile unit about the axis of rotation.

14. The drive module according to claim 12, wherein the circular element consists of a flexible endless belt following a generally C-shaped path centered on the axis of rotation and stationary relative to the mobile unit about said axis of rotation, the opening of the C defining an opening for unobstructed access to the access opening of the mobile unit, and having a radially outer side which engages with the control part in the active adjustment configuration and a radially inner side which engages with the transmission mechanism.

15. The drive module according to claim 9, wherein the transmission mechanism of the transmission part comprises a motor embedded in the mobile unit, and the motive power transfer system comprises a slip ring comprising a first portion that is part of the control part carried by the base and connected to an electrical power source, and a second portion that is part of the transmission part and connected to the motor, the first portion and second portion being maintained in sliding contact regardless of the relative orientation of the mobile unit and the base about the axis of rotation, when the control part is in the active adjustment configuration.

16. The drive module according to claim 1, wherein the translation driving means comprises, on each side of the receiving space:
at least first and second pulleys comprising a driving surface and carried by the mounting,
an elongate band constituting the drive element and comprising a first side and an opposite second side, the first side engaging with the driving surface of the pulleys, the second side constituting the driving surface adapted to engage with the flexible medical member, the band being tensioned between the pulleys with an elongate portion extending along the receiving space in the main direction,
and wherein the push surface of the push element is positioned between the first and second pulleys and engages with the first side of the band.

17. The drive module according to claim 1, wherein all of the parts are consumable and/or sterilizable items.

* * * * *